(12) United States Patent
Wang et al.

(10) Patent No.: US 11,485,966 B2
(45) Date of Patent: Nov. 1, 2022

(54) METHOD FOR IMPROVING LOADING AND STABILITY OF NUCLEIC ACID

(71) Applicants: MGI TECH CO., LTD., Shenzhen (CN); COMPLETE GENOMICS, INC., San Jose, CA (US)

(72) Inventors: Hui Wang, Shenzhen (CN); Xun Xu, Shenzhen (CN); Jin Yang, Shenzhen (CN); Ao Chen, Shenzhen (CN); Chongjun Xu, San Jose, CA (US); Wenwei Zhang, Shenzhen (CN)

(73) Assignees: MGI TECH CO., LTD., Guangdong (CN); COMPLETE GENOMICS, INC., San Jose, CA (US)

( * ) Notice: Subject to any disclaimer, the term of this patent is extended or adjusted under 35 U.S.C. 154(b) by 206 days.

(21) Appl. No.: 16/754,713

(22) PCT Filed: Oct. 11, 2017

(86) PCT No.: PCT/CN2017/105726
§ 371 (c)(1),
(2) Date: Apr. 8, 2020

(87) PCT Pub. No.: WO2019/071471
PCT Pub. Date: Apr. 18, 2019

(65) Prior Publication Data
US 2020/0255821 A1 Aug. 13, 2020

(51) Int. Cl.
*C12N 15/10* (2006.01)
*C12N 15/11* (2006.01)
*C12Q 1/68* (2018.01)

(52) U.S. Cl.
CPC .......... *C12N 15/1006* (2013.01); *C12N 15/11* (2013.01); *C12Q 1/68* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 5,424,413 A * | 6/1995 | Hogan | .................. | C12Q 1/6823 536/24.31 |
| 5,437,977 A * | 8/1995 | Segev | .................. | C12Q 1/6813 435/6.12 |
| 6,383,783 B1 * | 5/2002 | Haddad | .............. | C12N 15/1006 435/180 |
| 9,796,749 B2 * | 10/2017 | Yin | .......................... | C12Q 1/68 |
| 2004/0248161 A1 | 12/2004 | Rothberg et al. | | |
| 2007/0048759 A1 * | 3/2007 | Luo | .................. | C12Q 2525/313 435/6.19 |
| 2010/0090180 A1 * | 4/2010 | Chaikin | ................. | C12Q 1/682 252/582 |
| 2015/0299784 A1 * | 10/2015 | Fan | ...................... | C12Q 1/6876 506/4 |
| 2016/0010054 A1 * | 1/2016 | Gartner | ................ | C12N 5/0068 435/174 |
| 2017/0204477 A1 * | 7/2017 | Green | ................... | C12N 15/113 |
| 2018/0334711 A1 * | 11/2018 | Kelley | ................ | C12Q 1/6811 |
| 2019/0137484 A9 * | 5/2019 | Soldo | ................... | B01J 20/3248 |
| 2019/0203275 A1 * | 7/2019 | Frisen | ................. | C12Q 1/6876 |
| 2020/0255821 A1 * | 8/2020 | Wang | ....................... | C12Q 1/68 |

FOREIGN PATENT DOCUMENTS

| CN | 108018343 A | 5/2018 |
|---|---|---|
| WO | WO 2013/066975 A1 | 5/2013 |
| WO | WO 2013/169339 A1 | 11/2013 |
| WO | WO 2016/058517 A1 | 4/2016 |

OTHER PUBLICATIONS

Aboutaleb et al., Improvement of Domperidone Solubility and Dissolution Rate by Dispersion in Various Hydrophilic Carriers. J. of Applied Pharmaceutical Science 6(7):133-139 (Year: 2016).*
Kokalj et al., Building bio-assays with magnetic particles on a digital microfluidic platform. New Biotechnology 32(5) : 485 (Year: 2015).*
Liu et al., DNA Amplification and Hybridization Assays in Integrated Plastic Monolithic Devices. Analytical Chemistry 74 :3063-3070 (Year: 2002).*
Peng et al., Coupling oligonucleotides possessing a polycytosine tag with magnetic ionic liquids for sequence-specific DNA analysis. Chem. Comm 54 :10284-10287 (Year: 2018).*
Pluronic F-68 ; Selleckchem.com (Copyright 2013) (Year: 2013).*
Wang et al., Mitochondrial mechanisms of neuronal rescue by F-68, a hydrophilic Pluronic block co-polymer, following acute substrate deprivation. Neurochem. Int. 109:126-140 Oct. 1, 2018.*
Zhou et al,, A Compact Functional Quantum Dot-DNA Conjugate: Preparation, Hybridization, and Specific Label-Free DNA Detection. Langmuir 24:1659 (Year: 2008).*
Drmanac et al., Human Genome Sequencing using Unchained Base Reads on Self-assembling DNA Nanoarrays. Science 327 : 78 (Year: 2010).*
Mak et al., "Comparative performance of the BGISEQ-500 vs Illumina HiSeq2500 sequencing platforms for palaeogenomic sequencing", GigaScience, 2017, 6: 1-13.
Nam et al., "Role of phosphate-modified mesoporous silica nanoparticles for altering biomimetic metal-induced aggregation process of pluronic F127 block copolymer", Materials Letters, 2013, 110: 176-179.

* cited by examiner

*Primary Examiner* — Ethan C Whisenant
(74) *Attorney, Agent, or Firm* — James S. Keddie; Bozicevic, Field & Francis LLP

(57) ABSTRACT

The present invention provides a method for improving the loading of nucleic acid on a solid support by contacting the solid support with a poloxamer-containing reagent. The present invention also provides a method for improving the stability of a nucleic acid on a solid support, comprising contacting a nucleic acid molecule with a partially double-strand oligonucleotide before or after loading the nucleic acid molecule on a solid support, so as to cause the nucleic acid molecule to hybridize with the oligonucleotide. The present invention also provides a combined use of the two methods.

20 Claims, 4 Drawing Sheets
Specification includes a Sequence Listing.

METHOD FOR IMPROVING LOADING AND STABILITY OF NUCLEIC ACID

CROSS-REFERENCE TO RELATED APPLICATIONS

This application is a § 371 national phase of International Application No. PCT/CN2017/105726, filed on Oct. 11, 2017, which application is incorporated by reference herein.

TECHNICAL FIELD

The present invention relates to the field of nucleic acid sequencing. In particular, the present invention relates to a method for improving the loading of a nucleic acid on a solid support by contacting the solid support with a poloxamer-containing reagent. The present invention also relates to a method for improving the stability of a nucleic acid on a solid support, which comprises contacting the nucleic acid molecule with a partially double-stranded oligonucleotide to hybridize the nucleic acid molecule with the oligonucleotide before or after loading the nucleic acid molecule on the solid support.

BACKGROUND

Large-scale genomic sequence analysis is a key step in understanding many different biological phenomena. The need for low-cost, high-throughput sequencing and resequencing has enabled the development of new sequencing methods for simultaneous and parallel analysis of multiple nucleic acid targets.

In various sequencing methods, it is often necessary to load a nucleic acid target to be sequenced on a solid support. However, in conventional sequencing methods, there are many problems in loading a nucleic acid on a solid support, such as poor loading uniformity and poor stability of nucleic acid after loading.

Therefore, there is a need for an improved method to promote the uniform and stable loading of a nucleic acid on a solid support.

CONTENTS OF INVENTION

The present invention relates to a method for improving the attachment (i.e., loading or immobilization) of a nucleic acid to a solid support. Generally, such method comprises contacting a solid support with a poloxamer-containing reagent. In some embodiments, the present invention relates to a method for improving the stability of a nucleic acid on a solid support, comprising contacting the nucleic acid molecule with a partially double-stranded oligonucleotide to hybridize the nucleic acid molecule with the oligonucleotide before or after loading the nucleic acid on the solid support. In other embodiments, the present invention also relates to a combined use of these two methods.

In the course of making the present invention, the inventors have surprisingly found that treating a solid support with a poloxamer-containing reagent could significantly improve the loading of nucleic acids (such as DNA nanoballs (DNBs)) on the solid support. In particular, the uniformity of loading nucleic acids (such as DNBs) on the solid support was significantly improved, thereby significantly improving signal-to-noise ratio (SNR) and FIT values (which indicated the discrimination of each base) in a subsequent nucleic acid analysis, for example.

Accordingly, in one aspect, the present invention provides a method for improving loading of a nucleic acid (e.g., DNB) on a solid support, comprising a) providing a solid support having a nucleic acid immobilized thereon, and b) allowing the solid support to contact with a poloxamer-containing reagent (e.g., an aqueous solution). In one embodiment, the method comprises, in step a), providing the solid support having the nucleic acid immobilized thereon in the presence of poloxamer.

In one aspect, the present invention provides a method for loading a nucleic acid (such as a DNA nanoball) on a solid support, comprising a) providing a solid support having a nucleic acid immobilized thereon, and b) allowing the solid support to contact with a poloxamer-containing reagent (e.g., aqueous solution). In one embodiment, the method comprises, in step a), providing the solid support having the nucleic acid immobilized thereon in the presence of poloxamer.

As used herein, loading a nucleic acid on a solid support means immobilizing or attaching the nucleic acid molecule to the solid support. Such immobilization or attachment may be in a covalent or non-covalent manner.

The term "nucleic acid" as used herein can be used interchangeably with "nucleic acid molecule", "polynucleotide", "oligonucleotide", "target nucleic acid", which can be any type of nucleic acid, for example, the nucleic acid can be deoxyribonucleic acid (DNA), ribonucleic acid (RNA), or an analog of DNA or RNA made from nucleotide analogs. The nucleic acid can be single-stranded, double-stranded, or contain both single- and double-stranded sequences. The nucleic acid molecule may be derived from a double-stranded DNA (dsDNA) form (e.g., genomic DNA, product of PCR and amplification, etc.), or may be derived from a single-stranded form such as DNA (ssDNA) or RNA that may be converted into a dsDNA form, and vice versa. In some embodiments, the immobilized nucleic acid can be in the form of a single molecule (which can be a natural molecule, a modified molecule such as a labeled molecule, or a nucleic acid including a nucleotide analog), a concatamer of a sequence (e.g., a nucleic acid nanoball described in detail herein, etc.), can be amplified (e.g., amplified as concatamers, amplified as multiple individual molecules with the same or similar sequences, etc.), and/or can be in any other forms. The exact sequence of the nucleic acid molecule may be known or unknown. The following are illustrative examples of the nucleic acid: gene or gene fragment (e.g., probe, primer, EST or SAGE tag), genomic DNA, genomic DNA fragment, exon, intron, messenger RNA (mRNA), transit RNA, ribosomal RNA, ribozyme, cDNA, nucleic acid library, recombinant polynucleotide, synthetic polynucleotide, branched polynucleotide, plasmid, vector, isolated DNA of any sequence, isolated RNA of any sequence, nucleic acid probe, primer or amplified copy of any of the above sequences.

The nucleic acid may include nucleotide or nucleotide analog. The nucleotide usually comprises a saccharide, a nucleobase, and at least one phosphate group. The nucleotide can be free of base (i.e., lacking nucleobase). The nucleotides include deoxyribonucleotides, modified deoxyribonucleotides, ribonucleotides, modified ribonucleotides, peptide nucleotides, modified peptide nucleotides, nucleotides with a modified phosphate saccharide backbone and mixtures thereof. Examples of nucleotides include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP). Nucleotide analogs comprising modified nucleobases can also be used in the methods described herein. Whether having a natural backbone or a similar structure, exemplary modified nucleobases that can be comprised in a polynucleotide include, for example, inosine, xanthine, hypoxanthine, isocytosine, isoguanine, 2-aminopurine, 5-methylcytosine, 5-hydroxymethylcytosine, 2-aminoadenine, 6-methyladenine, 6-methylguanine, 2-propylguanine, 2-propyladenine, 2-thiouracil, 2-thiothymine, 2-thiocytosine, 15-halouracil, 15-halocytosine, 5-propynyluracil, 5-propynylcytosine, 6-azouracil, 6-azocytosine, 6-azothymine, 5-uracil, 4-thiouracil, 8-halo-adenine or guanine, 8-amino-adenine or guanine, 8-thio-adenine or guanine, 8-sulfanyl-adenine or guanine, 8-hydroxy-adenine or guanine, 5-halogen-substituted uracil or cytosine, 7-methylguanine, 7-methyladenine, 8-azaguanine, 8-azaadenine, 7-deazaguanine, 7-deazaadenine, 3-deazaguanine, 3-deazaadenine, etc. As known in the art, certain nucleotide analogs cannot be introduced into a polynucleotide, for example, nucleotide analogs, such as adenosine 5'-phosphoryl sulfate.

The nucleic acid molecule used in a specific embodiment of the present invention may have any length. In general, exemplary lengths of useful nucleic acids include, for example, at least about 5, 10, 20, 30, 40, 50, 60, 70, 80, 90, 100, 150, 200, 300, 400, 500, 1,000, 5,000 or 10,000, 100,000 nucleotides or longer. Alternatively, or in addition, the length may be no longer than 1,000,000, 100,000, 10,000, 1,000, 100 nucleotides or less. The length of the nucleic acid molecule may also include all integers between the above exemplary numbers. Thus, nucleic acids that can be sequenced using the methods described herein can, for example, be within the scope of short polynucleotides, fragments, cDNAs, genes, and genomic fragments.

The nucleic acid molecules loaded on the solid support of the present invention can be of any number, for example, can be 2, 3, 4, 5, 6, 7, 8, 9, 10, 20, 30, 40, 50, 60, 70, 80, 90 or 100 or more identical or different nucleic acid molecules. The number of nucleic acid molecules can also be, for example, 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, or $1\times10^7$ or more identical or different nucleic acid molecules. The number of nucleic acid molecules may also include all integers between the above exemplary numbers.

The nucleic acid can be obtained from any source. For example, the nucleic acid can be prepared from a nucleic acid molecule obtained from an organism, or a population of nucleic acid molecules obtained from one or more natural sources of organisms. The sources of nucleic acid molecules include, but are not limited to, organelles, cells, tissues, organs, or organisms. The cells that can be used as a source of nucleic acid molecules can be of prokaryotic (e.g., bacteria); or of eukaryotic, such as fungi (e.g., yeast), plants, protozoa and other parasites, and animals (including insects, nematodes), and mammals (e.g., rat, mouse, monkey, non-human primates, and human)); or the nucleic acid molecule may be derived from a virus.

In some embodiments, the nucleic acid can be obtained from a particular biological source. In a preferred embodiment, the nucleic acid is a human nucleic acid obtained from a human, for example, a sample of human tissue. In another preferred embodiment, the nucleic acid is a human mitochondrial nucleic acid. In another preferred embodiment, the nucleic acid can be obtained from a metagenomic sample. In other embodiments, the nucleic acid can be obtained from an environmental source that no longer contains a living organism.

As used herein, the terms "loading", "immobilization", and "attachment" when used for nucleic acids, mean direct or indirect attachment to a solid support via a covalent or non-covalent bond. In certain embodiments of the present disclosure, the method of the present invention comprises immobilizing a nucleic acid on a solid support via covalent attachment. But generally, all that is required is that the nucleic acid remains immobilized or attached to the solid support under conditions where it is desired to use the solid support (e.g., in applications that require nucleic acid amplification and/or sequencing). In certain embodiments, immobilizing a nucleic acid on a solid support can comprise immobilizing an oligonucleotide to be used as a capture primer or amplification primer on the solid support such that the 3' end is available for enzymatic extension and at least a portion of the primer sequence is capable of hybridizing to a complementary nucleic acid sequence; the nucleic acid to be immobilized is then hybridized with the oligonucleotide, in which case the immobilized oligonucleotide or polynucleotide may be 3'-5' direction. In certain embodiments, immobilizing a nucleic acid on a solid support can comprise binding a nucleic acid-binding protein to a solid support by amino modification and capturing the nucleic acid molecule through the nucleic acid-binding protein. Alternatively, the loading may occur by means other than base-pair hybridization, for example by covalent attachment as described above. Non-limiting examples of how the nucleic acids are attached to the solid support include nucleic acid hybridization, biotin-streptavidin binding, thiol binding, photoactivation binding, covalent binding, antibody-antigen, physical constraint via hydrogel or other porous polymers, etc. Various exemplary methods for immobilizing a nucleic acid on a solid support can be found, for example, in G. Steinberg-Tatman et al., Bioconjugate Chemistry 2006, 17, 841-848; Xu X. et al. Journal of the American Chemical Society 128 (2006) 9286-9287; US patent applications U.S. Pat. Nos. 5,639,603, 5,641,658, US2010248991; international patent applications WO2001062982, WO2001012862, WO2007111937, WO0006770, for all purposes, especially for all relevant teachings for the preparation of solid supports with nucleic acids immobilized thereon, the above documents are incorporated herein by reference in their entirety. In an embodiment of the present invention, the nucleic acid can be immobilized on a solid support in the presence of poloxamer.

As used herein, the term "solid support" means any insoluble substrate or matrix to which a nucleic acid can be attached, such as, for example, latex beads, dextran beads, polystyrene surfaces, polypropylene surfaces, polyacrylamide gels, gold surfaces, glass surfaces, chips, sensors, electrodes, and silicon wafers. The surface of the solid support may be of any desired shape, including, for example, planar, spherical or porous suitable for a particular application. For example, the solid support may be a planar glass surface.

In certain embodiments, the solid support may include an inert substrate or matrix, and the substrate or matrix has been chemically functionalized, for example, by applying a layer or coating of an intermediate material, in which the intermediate material has a reactive group allowing covalent attachment to a polynucleotide. The intermediate material may be directly or indirectly attached to the solid support via a covalent or non-covalent bond. As a non-limiting example for non-covalent attachment to the solid support, such support may comprise a polyacrylamide hydrogel layer on an inert substrate such as glass. In such embodiments, the polynucleotide (e.g., a nucleic acid molecule to be sequenced) can be directly covalently attached to an intermediate layer (e.g., a hydrogel), but the intermediate layer itself can be non-covalently attached to another substrate or matrix (such as a glass substrate) layer.

As used herein, the term "poloxamer" refers to a block copolymer formed from a polyoxypropylene chain flanked by two polyoxyethylene chains. Poloxamer is available for sale under the trade names PLURONIC® (BASF), KOLLIPHOR® (BASF), LUTROL® (BASF) and SYNPERONIC® (Croda International). Unless a specific poloxamer variety is specified, "poloxamer" as mentioned may refer to various poloxamer varieties.

As used herein, a "poloxamer-containing reagent" may be a poloxamer-containing aqueous solution or other suitable solution such as an organic solution, such as an ethanol, ethyl acetate, or chloroform solution. It should be understood that such a solution should not affect the properties of poloxamer and should not have any adverse effects on the solid support, nucleic acid molecules, oligonucleotides, and binding of the nucleic acid to the solid support as described herein. The concentration of poloxamer in the reagent or solution can be any concentration commonly used for poloxamer. In some embodiments, the concentration of poloxamer in the reagent or solution can be about 0.01% to about 2%, or about 0.05% to about 1%, or about 0.1% to about 0.5%, or about 0.2% to about 0.5%, or about 0.3% to about 0.5%, or about 0.4% to about 0.5% (w/v). In a preferred embodiment, the concentration of poloxamer in the reagent or solution can be about 0.1%, about 0.2%, about 0.3%, about 0.4%, or about 0.5% (w/v). In other embodiments, the concentration of poloxamer in the reagent or solution can also be less than about 0.01% or greater than about 2%. In certain embodiments, the poloxamer-containing reagent also comprises a buffering agent. Suitable buffering agents can be easily determined by those skilled in the art. Suitable buffering agents may include, for example, organic salts to maintain a stable pH of about pH 6 to pH 9, and may also contain monovalent or divalent cations or detergents to remove non-specifically bound molecules from the solid support. Exemplary buffers may include, for example, Tris-HCl buffer (e.g., 100 mM Tris-HCl buffer at pH 6.5), SSC buffer (e.g., 0.3×SSC/0.1% Tween), TE buffer (e.g., TE buffer containing 10 mM Tris-HCl and 1 mM EDTA at pH8) and buffers as used in the examples of this application.

The term "poloxamer" may encompass many different compounds because polyoxypropylene and polyoxyethylene chains of different lengths can be used in combination. The specific combination of polyoxypropylene and polyoxyethylene chains present in poloxamer can produce specific chemical and/or biophysical properties. In some embodiments, poloxamer has the chemical formula of $HO(C_2H_4O)_n(C_3H_6O)_m(C_2H_4O)_nH$. In some embodiments, n (i.e., the polyoxyethylene chain length) has a value of about 60 to about 150. In some embodiments, m (i.e., the polyoxypropylene chain length) has a value of about 25 to about 60.

Poloxamer is often described by a numbering system that indicates their approximate molecular weight and percentage of polyoxyethylene content. These values may refer to the average values in a poloxamer composition, rather than the absolute values of each poloxamer molecule in the composition. According to this system, multiplying the first two numbers by 100 gives the approximate molecular weight of the polyoxypropylene block, and multiplying the third number by 10 gives the weight percentage of the polyoxyethylene block. For example, poloxamer 188 (CAS No. 9003-11-6) may refer to a poloxamer in which n has a value of about 80 and m has a value of about 27 in the above molecular formula. Poloxamer 237 may refer to a poloxamer where n has a value of about 64 and m has a value of about 37. Poloxamer 338 may refer to a poloxamer where n has a value of about 141 and m has a value of about 44. Poloxamer 407 may refer to a poloxamer where n has a value of about 101 and m has a value of about 56. In some embodiments, the poloxamer has an average molecular weight of from about 6,000 to about 18,000 Daltons. In some embodiments, the poloxamer 188 may refer to a poloxamer in which n has a value of about 80 and m has a value of about 27 in the above formula, and the poloxamer has an average molecular weight of about 7680 to about 9510 g/mol. In some embodiments, poloxamer 188 may refer to a poloxamer in which n has a value of about 80 and m has a value of about 27 in the above formula, and the poloxamer has an average molecular weight of about 7000 to about 10,000 g/mol.

A poloxamer sold under a brand name can be named according to different systems, for example, PLURONIC@. The letters can be used to indicate a physical state (for example, F means solid, P means paste, or L means liquid). Two or three numbers can be used to indicate chemical properties. The first or first two numbers are multiplied by 300 to give the approximate molecular weight of the polyoxypropylene block, and the third number is multiplied by 10 to give the weight percentage of the polyoxyethylene block. For example, PLURONIC@ F68 (PF68) may refer to a solid poloxamer in which n has a value of about 80 and m has a value of about 27 in the above formula. PLURONIC@ F87 (PF108) may refer to a solid poloxamer where n has a value of about 64 and m has a value of about 37. PLURONIC@ F108 (PF127) may refer to a solid poloxamer where n has a value of about 141 and m has a value of about 44. PLURONIC@ F127 may refer to a solid poloxamer where n has a value of about 101 and m has a value of about 56.

Since poloxamers may have hydrophobic (polyoxypropylene) and hydrophilic (polyoxyethylene) moieties of various lengths, different poloxamers may have different hydrophilic-lipophilic balance (HLB) values. The HLB of a compound can be determined by calculating the relative ratio of hydrophilic or lipophilic compound, and the HLB value can be used to predict the surfactant characteristics of the compound. For example, compounds with HLBs below 10 are predicted to be water-insoluble, while compounds with HLBs above 10 are predicted to be water-soluble. The HLB of poloxamer can be calculated according to methods well known in the art, including those disclosed by Griffin, WC (1954) J. Soc. Cosmet. Chemists 5 (4): 249-56, and Davies, J T (1957) Gas/Liquid and Liquid/Liquid Interfaces: Proc. of $2^{nd}$ Intl. Congress Surface Activity, Butterworths (London): 426-38.

In some embodiments, the physical and/or chemical properties of poloxamer can be measured. Examples of tests to measure physical and/or chemical properties include, but are not limited to, MALDI-MS, Gel Permeation Chromatography, powder-XRD, quasi-elastic light scattering, and solid state NMR.

In various embodiments of the present invention, the solid support is preferably treated with a hydrophilic poloxamer. The hydrophilic poloxamer is preferably a solid poloxamer dissolved in a liquid or an aqueous solution. As used herein, a hydrophilic poloxamer is preferably a poloxamer compound having an HLB greater than or equal to 10.

In an embodiment of the present invention, the solid support is preferably treated with a hydrophilic poloxamer having an HLB of 20-29 or a mixture thereof.

In other embodiments of the present invention, other hydrophilic poloxamers can also be used to treat the solid support, such as hydrophilic poloxamers having an HLB of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or higher or mixtures thereof.

In an embodiment of the present invention, it is preferred to treat the solid support with a poloxamer selected from the group consisting of PF68, PF108, PF127, equivalents and mixtures thereof. The equivalent of PF68, PF108 or PF127 means a poloxamer that is not sold under the trade name PLURONIC@ but has the same structure as PF68, PF108 or PF127.

According to another aspect of the present invention, the present invention provides a method for improving the stability of a nucleic acid on the solid support during nucleic acid analysis. In general, when a nucleic acid is loaded on a solid support and used for subsequent nucleic acid analysis, there is often a problem that the nucleic acid molecule is not stable enough. For example, the loading of nucleic acid is unstable, which causes the nucleic acid molecule to fall off, or the structure of the nucleic acid molecule loaded on the solid support is unstable and easily damaged. In the course of making the present invention, the inventors have surprisingly found that before or after loading a nucleic acid (such as DNB) on a solid support, allowing the partially double-stranded oligonucleotide of the present invention to contact with and hybridize to the nucleic acid to be analyzed (such as DNB), can significantly improve the stability of nucleic acid (such as DNB), thereby significantly reducing signal attenuation, for example, in subsequent nucleic acid analysis.

Accordingly, in some embodiments, the present invention provides a partially double-stranded oligonucleotide comprising a first oligonucleotide strand and a second oligonucleotide strand, wherein the first oligonucleotide strand from 5' to 3' contains region A and region B, and the second oligonucleotide strand from 5' to 3' contains region A' and region B', wherein the regions A and A' are reversely complementary to each other, and the region B and B' are not complementary to each other and each complementary to a predetermined target sequence (e.g., in a target nucleic acid) (thus the regions B and B' are also referred to as target binding regions), wherein the first oligonucleotide strand and the second oligonucleotide strand hybridize to each other through the regions A and A', thereby forming the partially double-stranded oligonucleotide. In a preferred embodiment, the regions B and B' are located at the 3' ends of the first oligonucleotide strand and second oligonucleotide strand, respectively.

In some embodiments of the present invention, the regions B and B' may be designed to be complementary to the same target sequence in a target nucleic acid. In other embodiments, the regions B and B' may be designed to be complementary to different target sequences in a target nucleic acid, or the regions B and B' may be designed to be complementary to different target nucleic acids.

In some embodiments of the present invention, the first oligonucleotide strand may further comprise a region C located at upstream of the region A, or the second oligonucleotide strand may further comprise a region C' located at upstream of the region A'. The region C or C' may be designed such that when a second partially double-stranded oligonucleotide is present, the region C or C' of the first partially double-stranded oligonucleotide is complementary in reverse to the region C or C' of the second partially double-stranded oligonucleotide respectively, so that the first partially double-stranded oligonucleotide and the second partially double-stranded oligonucleotide can hybridize to each other through the respective region C or C'.

In a preferred embodiment, the first oligonucleotide strand may further comprise a region C located at upstream of the region A, and the second oligonucleotide strand may further comprise a region C' located at upstream of the region A', wherein the regions C and C' are not complementary to each other. The regions C and C' may be designed such that when a second partially double-stranded oligonucleotide is present, at least one of the regions C and C' of the first partially double-stranded oligonucleotide is complementary in reverse to at least one of the regions C and C' of the second partially double-stranded oligonucleotide, so that the first partially double-stranded oligonucleotide and the second partially double-stranded oligonucleotide can hybridize to each other through the respective region C and/or C'. In a preferred embodiment, the regions C and C' may have the same or different sequences.

Thus, in some embodiments, the present invention also provides a group of partially double-stranded oligonucleotides, comprising at least two partially double-stranded oligonucleotides as described herein, wherein each of the partially double-stranded oligonucleotides comprises a first oligonucleotide strand and a second oligonucleotide strand, and the first oligonucleotide strand comprises a region C, a region A, and a region B from 5' to 3', and the second oligonucleotide strand comprises a region A' and a region B' from 5' to 3', wherein the region A and the region A' are reversely complementary to each other, and the region B and the region B' are not complementary to each other but each complementary to a predetermined target sequence, wherein the first oligonucleotide strand and the second oligonucleotide strand hybridize to each other through the regions A and A', thereby forming the partially double-stranded oligonucleotide, wherein the region C of at least one partially double-stranded oligonucleotide is reversely complementary to the region C of at least one other partially double-stranded oligonucleotide such that at least two partially double-stranded oligonucleotides can hybridize to each other through respective region C.

In other embodiments, the present invention also provides a group of partially double-stranded oligonucleotides comprising at least two partially double-stranded oligonucleotides as described herein, wherein each of the partially double-stranded oligonucleotides comprises a first oligonucleotide strand and a second oligonucleotide strand, the first oligonucleotide strand comprises a region C, a region A and a region B from 5' to 3', and the second oligonucleotide strand comprises a region C', a region A', and a region B' from 5' to 3', wherein the regions A and A' are complementary to each other in reverse, and the regions B and B' are not complementary to each other but each is complementary to a predetermined target sequence, wherein the first oligonucleotide strand and the second oligonucleotide strand hybridize to each other through the regions A and A', thereby forming the partially double-stranded oligonucleotide, wherein at least one of the regions C and C' of at least one partially double-stranded oligonucleotide is reversely complementary to at least one of the regions C and C' of at least one other partially double-stranded oligonucleotide such that at least two partially double-stranded oligonucleotides are capable of hybridizing to each other through respective regions C and/or C'. In a preferred embodiment, the regions C and C' may have the same or different sequences.

Without being bound by any theory, the inventors have surprisingly found that by using the partially double-stranded oligonucleotide or the group of partially double-stranded oligonucleotides of the present invention to hybridize to a target nucleic acid, more than one target nucleic acid can be indirectly correlated together through the partially double-stranded oligonucleotide of the present invention. This property is advantageous because, for example, in the case where the target nucleic acid is immobilized (i.e., loaded) on a solid support, this enables the target nucleic acid to be tightly bound to the solid support and is not susceptible to external forces that may destroy morphology and structure during nucleic acid analysis.

The partially double-stranded oligonucleotide or the group of partially double-stranded oligonucleotides of the present invention are also particularly suitable for use with a concatemer (e.g., DNA nanoball) comprising multiple target nucleic acid sequences. Without being bound by any theory, it is believed that when the partially double-stranded oligonucleotide or the group of partially double-stranded oligonucleotides of the present invention hybridizes to a concatemer comprising multiple target nucleic acid sequences, the target binding regions B and B' of the partially double-stranded oligonucleotide can hybridize to the individual target nucleic acid sequences, respectively, so that the individual target nucleic acid sequences are indirectly correlated together through the partially double-stranded oligonucleotide, so that the structure of the concatemer is more stable and less vulnerable to damage. In the case of using a group of partially double-stranded oligonucleotides of the present invention, since at least two of the partially double-stranded oligonucleotides therein can hybridize to each other, this enables more individual target nucleic acid sequences to be indirectly correlated together through the at least two partially double-stranded oligonucleotides, thereby further stabilizing the structure of the concatemer and making its structure less susceptible to damage. The multiple target nucleic acid sequences in the concatemer may be the same or different sequences. In a preferred embodiment, the multiple target nucleic acid sequences in the concatemer are the same sequence.

After hybridizing the partially double-stranded oligonucleotide as described herein to a nucleic acid molecule immobilized on a solid support (e.g., a nucleic acid nanoball, such as DNB), the partially double-stranded oligonucleotide as described herein also can be used as a primer for replication of a target nucleic acid.

In the embodiment of the present invention, the sequences of the regions A and A' of the partially double-stranded oligonucleotide as described herein are not particularly limited as long as they do not affect the hybridization between the regions B and B' and the target sequence as well as the hybridization between the partially double-stranded oligonucleotides through the regions C and/or C'. The lengths of the regions A and A' are not particularly limited, but are generally about 4 nucleotides to about 50 nucleotides in length, about 4 nucleotides to about 45 nucleotides in length, and about 4 nucleotides to about 40 nucleotides in length, about 4 nucleotides to about 35 nucleotides in length, about 4 nucleotides to about 30 nucleotides in length, about 4 nucleotides to about 25 nucleotides in length, or about 4 nucleotides to about 25 nucleotides in length. In some embodiments, the regions A and/or A' are 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In a preferred embodiment, the regions A and/or A' are about 15 to 30 nucleotides in length.

The lengths of the target binding regions B and B' of the partially double-stranded oligonucleotide as described herein are not particularly limited, and are generally about 4 nucleotides to about 70 nucleotides in length, and about 4 nucleotides to about 60 nucleotides in length, about 4 nucleotides to about 50 nucleotides in length, about 4 nucleotides to about 40 nucleotides in length, about 4 nucleotides to about 30 nucleotides in length, about 4 nucleotides to about 20 nucleotides in length, or about 4 nucleotides to about 10 nucleotides in length. In some embodiments, the target binding regions B and/or B' are 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60 or 70 or more nucleotides in length. A suitable length varies depending on the use of the oligonucleotide. For example, when the partially double-stranded oligonucleotide as described herein is used as a primer, the target binding regions B and/or B' may be about 30 to 42 nucleotides in length. In an embodiment of the present invention, the target binding regions B and B' of the first oligonucleotide strand and second oligonucleotide strand may be the same or different in length. In a preferred embodiment, the target binding regions B and B' of the first oligonucleotide strand and second oligonucleotide strand are the same in length.

The lengths of the regions C and C' of the partially double-stranded oligonucleotide as described herein are not particularly limited, and are generally about 4 nucleotides to about 70 nucleotides in length, about 4 nucleotides to about 60 nucleotides in length, about 4 nucleotides to about 50 nucleotides in length, about 4 nucleotides to about 40 nucleotides in length, about 4 nucleotides to about 30 nucleotides in length, about 4 nucleotides to about 20 nucleotides in length, or about 4 nucleotides to about 10 nucleotides in length. In some embodiments, the regions C and/or C' are 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, or 70 or more nucleotides in length. In a preferred embodiment, the regions C and/or C' are about 20 to 50 nucleotides in length.

As used herein, the term "primer" refers to a polynucleotide that can serve as a starting point for nucleic acid template synthesis in a suitable buffer and at a suitable temperature under suitable conditions (that is, in the presence of 4 different nucleoside triphosphates and reagents for polymerization, such as DNA or RNA polymerase or reverse transcriptase). Thus, the primer comprises a target binding region that hybridizes to a target nucleic acid (template) (e.g., a target binding region of the partially double-stranded oligonucleotide as described herein). The primer is generally an oligonucleotide and is single-stranded. However, the primer may refer to a polynucleotide with a double-stranded segment (e.g., the partially double-stranded oligonucleotide as described herein). A suitable length of the target binding region suitable for the primer depends on the intended use of the primer. A short primer molecule typically requires a lower temperatures to form a sufficiently stable hybrid complex with the template. The primer does not need to reflect the exact sequence of the nucleic acid template, but must be sufficiently complementary so as to hybridize to the nucleic acid template. In the context, the primer generally refers to the partially double-stranded oligonucleotide as described herein.

As used herein, the term "target nucleic acid" refers to a nucleic acid to be detected or to be used as a template for priming (e.g., PCR or random priming). The target nucleic acid may be single-stranded or double-stranded, although for the applications described herein, generally known methods are used to make the double-stranded target nucleic acid single-stranded. The target nucleic acid may include, for example, polynucleotides of prokaryotes, eukaryotes or viruses with nucleic acids from substantially any natural source (e.g., cells, tissue or biological fluids). As conventionally used in the art, the target nucleic acid may also contain an adaptor sequence with known sequence to facilitate its amplification or sequencing.

As used herein, a "region" or "zone" of nucleic acid is a continuous segment of nucleotides of any length.

As used herein, the term "target binding region" refers to a nucleic acid segment that is complementary to a target nucleic acid.

As used herein, the terms "complementary" or "substantially complementary" refer to hybridization or base-pairing or duplex formation between nucleotides or nucleic acids (e.g., between two strands of a double-stranded DNA molecule, or between a target binding region on a single-stranded nucleic acid and a target nucleic acid). If a nucleotide of one nucleic acid can form a hydrogen bond with a nucleotide of another nucleic acid at a given position, the two nucleic acids are considered to be complementary to each other at that position. Complementary nucleotides are typically A and T (or A and U), or C and G. When optimal alignment and comparison is conducted and nucleotide insertions or deletions are appropriately considered, if at least about 80%, usually at least about 90% to about 95%, even about 98% to 100% of the nucleotides of one strand are paired to the other one, the two single-stranded RNA or DNA molecules are considered to be substantially complementary.

As used herein, the term "hybridization" refers to sufficient hydrogen bonding between complementary nucleotides or nucleotide bases, which can be, for example, Watson-Crick, Hoogsteen or reverse Hoogsteen hydrogen bonding to allow a stable and specific binding between the nucleic acid strands. Hybridization capacity is determined according to stringent conditions (comprising appropriate buffer concentration and temperature, which allow specific hybridization to a target nucleic acid with a fully or partially complementary region). Therefore, not all nucleotides of a nucleic acid need to be complementary. In addition, a nucleic acid strand is "substantially complementary" when it hybridizes to all, part, or an overlapping region of a target nucleic acid. Qualitative and quantitative considerations for establishing stringent hybridization conditions for designing the oligonucleotides or primers of the present invention are known in the art, see, for example, Ausubel et al., Short Protocols in Molecular Biology (4$^{th}$ ed., John Wiley & Sons 1999); Sambrook et al., Molecular Cloning: A Laboratory Manual (3$^{rd}$ ed., Cold Spring Harbor Laboratory Press 2001): Nucleic Acid Hybridisation: A Practical Approach (B D Hames & S J Higgins eds., IRL Press 1985).

As used herein, the term "$T_m$" generally refers to a temperature at which half of double-stranded nucleic acid molecules are dissociated into single strands. The formula for calculating the $T_m$ of a nucleic acid is well known in the art. As the standard reference points out, when a nucleic acid is in an aqueous solution with a cation concentration of 0.5M or less, its $T_m$ value can be simply estimated by the formula: $T_m$=81.5+16.6(log 10[Na$^+$])0.41(%[G+C])−675/n−1.0 m, wherein (G+C) content is between 30% and 70%, n is the number of bases, and m is the percentage of mismatched base pairs (see, for example, Sambrook J et al. (2001), Molecular Cloning, A Laboratory Manual, (3$^{rd}$ Ed., Cold Spring Harbor Laboratory Press). Other references provide more complex calculation methods that take structural and sequence characteristics into account when calculating $T_m$ (see also, Anderson and Young (1985), Quantitative Filter Hybridization, Nucleic Acid Hybridization, and Allawi and Santa Lucia (1997), Biochemistry 36: 10581-94).

In embodiments of the invention, before or after loading a target nucleic acid (e.g., DNB) on a solid support, the partially double-stranded oligonucleotide or the group of partially double-stranded oligonucleotides as described herein is used to contact with and hybridize to a nucleic acid to be analyzed (e.g., DNB), which can significantly improve the stability of the nucleic acid (e.g., DNB), thereby significantly reducing signal attenuation, for example, in subsequent nucleic acid analysis.

Thus, in one embodiment, the present invention provides a method for improving the stability of a nucleic acid on a solid support, comprising the following steps of: a) providing a solid support having a nucleic acid molecule immobilized thereon; and b) allowing the partially double-stranded oligonucleotide or the group of partially double-stranded oligonucleotides as described herein to hybridize to the nucleic acid molecule on the solid support, wherein the partially double-stranded oligonucleotide hybridizes through the regions B and/or B' to the nucleic acid molecule.

In another embodiment, the present invention provides a method for improving the stability of a nucleic acid on a solid support, comprising the following steps of: a) providing a nucleic acid molecule; b) allowing the partially double-stranded oligonucleotide or the group of partially double-stranded oligonucleotides as described herein to hybridize to the nucleic acid molecule, wherein the partially double-stranded oligonucleotide hybridizes through the regions B and/or B' to the nucleic acid molecule; and c) immobilizing the nucleic acid molecule on the solid support.

In an embodiment of the present invention, after the target binding region B and/or B' of the partially double-stranded oligonucleotide as described herein is hybridized to a target nucleic acid, the target nucleic acid can be used as a template, and a complementary nucleic acid strand can be synthesized from the 3' end of the target binding region B and/or B' under the catalysis of a polymerase. Therefore, in some embodiments, the method of the present invention may further comprise synthesizing a complementary nucleic acid strand from the 3' end of the target binding region B and/or B' using the nucleic acid molecule on the solid support as a template in the presence of a polymerase. In other embodiments, the partially double-stranded oligonucleotide as described herein can hybridize to a target nucleic acid without being used as a primer to initiate the nucleic acid synthesis.

Suitable hybridization conditions for the partially double-stranded oligonucleotide as described herein are known in the art, see, for example, Sambrook et al., idem; Ausubel, et al., idem. See also Tijssen, Laboratory Techniques in Biochemistry and Molecular Biology, Vol. 24: Hybridization with Nucleic Acid Probes (Elsevier, N.Y. 1993). Hybridization is usually performed under stringent conditions that allow stable and specific binding of complementary nucleic acid strands and any washing conditions that can remove non-specific binding of oligonucleotides. Generally, stringent hybridization occurs at a temperature in the range of about 5° C. below the melting temperature (Tm) of the oligonucleotide to about 20° C. to 25° C. below the Tm. The stringency can be increased or decreased so as to specifically bind a target nucleic acid that is 100% complementary, or to bind a related nucleotide sequence that is less than 100% complementary. In some methods, very stringent conditions are set as equal to the Tm of a particular oligonucleotide. The factors such as the length and nature of sequence (DNA, RNA, base composition), the nature of target nucleic acid (DNA, RNA, base composition, present in solution or immobilized), and concentrations of salts and other components (e.g., presence or absence of formamide, dextran sulfate, and/or polyethylene glycol) are considered, and hybridization solution can be altered to produce lowly, moderately, or highly stringent conditions. The washing conditions are generally from room temperature to 60° C.

For example, highly stringent conditions may comprise, for example, a hybridization step in 6×NaCl/sodium citrate (SSC) at about 45° C., followed by washing with 2×SSC at 50° C.; or, alternatively, for example, hybridization in 5×SSC, 20 mM NaPO$_4$, pH 6.8, 50% formamide at 42° C., followed by washing with 0.2×SSC at 42° C. These conditions can vary depending on the composition and length of the nucleotide bases and the environment in which they are used, or vary empirically or based on a formula for determining such changes (see, for example, Sambrook et al., idem; Ausubel et al., idem). Depending on the base composition, source and concentration of the target nucleic acid, other stringent conditions can be used, including, for example, lowly stringent conditions (for example, performed at 37-45° C. in 4-6×SSC/0.1-0.5% w/v SDS for 2 to 3 hours), or moderately stringent conditions (e.g., performed at 45° C. in 1-4×SSC/0.25-0.5% w/v SDS for 2 to 3 hours).

In some embodiments of the invention, the loading of a nucleic acid on a solid support can be further improved by using the partially double-stranded oligonucleotide as described herein in combination with a poloxamer-containing reagent. Preferably, a hydrophilic poloxamer is used, for example, a hydrophilic poloxamer having an HLB of 20-29 or a mixture thereof is used; preferably, a hydrophilic poloxamer selected from the group consisting of PF68, PF108, PF127, equivalents and mixtures thereof is used.

Accordingly, in some embodiments, the present invention provides a method for improving the loading and stability of a nucleic acid on a solid support, comprising the steps of: a) providing a solid support having a nucleic acid molecule immobilized thereon; b) allowing the solid support to contact with a poloxamer-containing reagent; and c) hybridizing the partially double-stranded oligonucleotide or the group of partially double-stranded oligonucleotides as described herein to the nucleic acid molecule on the solid support, wherein the partially double-stranded oligonucleotide hybridizes to the nucleic acid molecule through the regions B and/or B'. In some embodiments, the method comprises, in step a), providing a solid support having a nucleic acid molecule immobilized thereon in the presence of poloxamer. In some embodiments, step c) may be performed before step b).

In other embodiments, the present invention provides a method for improving the loading and stability of a nucleic acid on a solid support, comprising the steps of: a) providing a nucleic acid molecule; b) hybridizing the partially double-stranded oligonucleotide or the group of partially double-stranded oligonucleotides as described herein to the nucleic acid molecule, wherein the partially double-stranded oligonucleotide hybridizes to the nucleic acid molecule through the regions B and/or B'; c) immobilizing the nucleic acid molecule on the solid support; and d) contacting the solid support with a poloxamer-containing reagent. In some embodiments, the method comprises, in step c), immobilizing the nucleic acid molecule on a solid support in the presence of poloxamer.

In a preferred embodiment, the nucleic acid used in the method of the present invention to be immobilized on the solid support is a nucleic acid nanoball, such as a DNA nanoball (DNB).

Accordingly, in one embodiment, the present invention provides a method for improving the stability of a nucleic acid nanoball on a solid support, comprising: a) providing a solid support having a nucleic acid nanoball immobilized thereon; and b) hybridizing the partially double-stranded oligonucleotide or the group of partially double-stranded oligonucleotides as described herein to the nucleic acid nanoball on the solid support, wherein the partially double-stranded oligonucleotide hybridizes to the nucleic acid nanoball through the regions B and/or B'. In a preferred embodiment, each nucleic acid copy in the nucleic acid nanoball comprises a region complementary to the target binding region B and/or B' of the partially double-stranded oligonucleotide.

In one embodiment, the present invention provides a method for improving the stability of a nucleic acid nanoball on a solid support, comprising the steps of: a) providing a nucleic acid nanoball; b) hybridizing the partially double-stranded oligonucleotide or the group of partially double-stranded oligonucleotide as described herein to the nucleic acid nanoball, wherein the partially double-stranded oligonucleotide hybridizes to the nucleic acid nanoball through the regions B and/or B'; and c) immobilizing the nucleic acid nanoball on the solid support. In a preferred embodiment, each nucleic acid copy in the nucleic acid nanoball comprises a region complementary to the target binding region B and/or B' of the partially double-stranded oligonucleotide.

In one embodiment, the present invention provides a method for improving the loading and stability of a nucleic acid nanoball on a solid support, comprising the steps of: a) providing a solid support having a nucleic acid nanoball immobilized thereon; b) allowing the solid support to contact with a poloxamer-containing reagent; and c) hybridizing the partially double-stranded oligonucleotide or the group of partially double-stranded oligonucleotides as described herein to the nucleic acid nanoball on the solid support, wherein the partially double-stranded oligonucleotide hybridizes to the nucleic acid nanoball through the regions B and/or B'. In some embodiments, the method comprises, in step a), providing a solid support having a nucleic acid nanoball immobilized thereon in the presence of poloxamer. In some embodiments, step c) may be performed before step b). In a preferred embodiment, each nucleic acid copy in the nucleic acid nanoball comprises a region complementary to the target binding region B and/or B' of the partially double-stranded oligonucleotide.

In one embodiment, the present invention provides a method for improving the loading and stability of a nucleic acid nanoball on a solid support, comprising the steps of: a)

providing a nucleic acid nanoball; b) hybridizing the partially double-stranded oligonucleotide or the group of partially double-stranded oligonucleotides as described herein to the nucleic acid nanoball, wherein the partially double-stranded oligonucleotide hybridizes to the nucleic acid nanoball through the regions B and/or B'; c) immobilizing the nucleic acid nanoball on the solid support; and d) contacting the solid support with a poloxamer-containing reagent. In some embodiments, the method comprises, in step c), immobilizing the nucleic acid nanoball on a solid support in the presence of poloxamer. In a preferred embodiment, each nucleic acid copy in the nucleic acid nanoball comprises a region complementary to the target binding region B and/or B' of the partially double-stranded oligonucleotide.

The term "nanoball" as used herein generally refers to a macromolecule or complex that has a compact (approximately) spherical shape, for example, having an internal diameter range typically between about 1 nm and about 1000 nm, preferably between about 50 nm and about 500 nm.

The term "nucleic acid nanoball" as used herein is generally a concatemer comprising multiple copies of a target nucleic acid molecule. These nucleic acid copies are typically arranged one after another in a continuous linear strand of nucleotides, but the nucleic acid nanoball of the present invention can also be made from any nucleic acid molecule using the methods described herein. This tandem repeat structure, along with the single-stranded nature of DNA, results in a nanoball folding configuration. Generally speaking, the multiple copies of a target nucleic acid molecule in a nucleic acid nanoball each contain an adaptor sequence of known sequence to facilitate amplification or sequencing. The adaptor sequence of each target nucleic acid molecule is usually the same, but it may be different as well. The nucleic acid nanoball typically includes DNA nanoball, also referred to herein as DNB (DNA nanoball).

The nucleic acid nanoball can be produced using, for example, rolling circle replication (RCR). The RCR process has been used to make multiple consecutive copies of the M13 genome (Blanco et al. (1989) J Biol Chem 264: 8935-8940). In this method, the nucleic acid is replicated by linear concatenation. A person skilled in the art can find guidance on the selection of conditions and reagents for the RCR reaction in a number of references, including U.S. Pat. Nos. 5,426,180, 5,854,033, 6,143,495 and 5,871,921, for all purposes, especially for all teachings regarding the preparation of nucleic acid nanoball by RCR or other methods, these documents are incorporated herein by reference in their entirety.

Generally, the components of RCR reaction include a single-stranded circular DNA, one or more primers capable of annealing with the circular DNA, a DNA polymerase having strand displacement activity to extend the 3' end of the primer annealing with the circular DNA, nucleoside triphosphates, and conventional polymerase reaction buffer. These components are combined under conditions that allow the primers to anneal to the circular DNA. These primers are extended by the DNA polymerase to form a concatemer of complementary strands of the circular DNA.

The method of forming the DNB of the present invention is disclosed in published patent applications WO2007120208, WO2006073504, WO2007133831 and US2007099208, as well as U.S. patent applications U.S. Ser. No. 60/992,485, U.S. 61/026,337, U.S. 61/035,914, U.S. 61/061,134, U.S. 61/116,193, U.S. 61/102,586, U.S. Ser. No. 12/265,593, U.S. Ser. No. 12/266,385, U.S. Ser. No. 11/938,096, U.S. Ser. No. 11/981,804, U.S. Ser. No. 11/981,797, U.S. Ser. No. 11/981,793, U.S. Ser. No. 11/981,767, U.S. Ser. No. 11/981,761, U.S. Ser. No. 11/981,730 (filed on Oct. 31, 2007), U.S. Ser. No. 11/981,685, U.S. Ser. No. 11/981,661, U.S. Ser. No. 11/981,607, U.S. Ser. No. 11/981,605, U.S. Ser. No. 11/927,388, U.S. Ser. No. 11/927,356, U.S. Ser. No. 11/679,124, U.S. Ser. No. 11/541,225, U.S. Ser. No. 10/547,214, U.S. Ser. No. 11/451,692 and U.S. Ser. No. 11/451,691, for all purposes, especially for all teachings relevant to formation of DNB, the entire contents of these documents are incorporated herein by reference in their entirety.

The nucleic acid nanoball can be loaded on the surface of solid support as described herein. The nanoball can be attached to the surface of solid support by any suitable method. Non-limiting examples of such methods include nucleic acid hybridization, biotin streptavidin binding, thiol binding, photoactive binding, covalent binding, antibody-antigen, physical constraints via hydrogels or other porous polymers, etc., or combinations thereof. In some cases, the nanoball can be digested with a nuclease (e.g., a DNA nuclease) to produce a smaller nanoball or a fragment from the nanoball.

The methods for loading the nucleic acid nanoball on a solid support are disclosed in published patent applications WO2007120208, WO2006073504, WO2007133831 and US2007099208, as well as U.S. patent applications U.S. Ser. No. 60/992,485, U.S. 61/026,337, U.S. 61/035,914, U.S. 61/061,134, U.S. 61/116,193, U.S. 61/102,586, U.S. Ser. No. 12/265,593, U.S. Ser. No. 12/266,385, U.S. Ser. No. 11/938,096, U.S. Ser. No. 11/981,804, U.S. Ser. No. 11/981,797, U.S. Ser. No. 11/981,793, U.S. Ser. No. 11/981,767, U.S. Ser. No. 11/981,761, U.S. Ser. No. 11/981,730, U.S. Ser. No. 11/981,685, U.S. Ser. No. 11/981,661, U.S. Ser. No. 11/981,607, U.S. Ser. No. 11/981,605, U.S. Ser. No. 11/927,388, U.S. Ser. No. 11/927,356, U.S. Ser. No. 11/679,124, U.S. Ser. No. 11/541,225, U.S. Ser. No. 10/547,214, U.S. Ser. No. 11/451,692 and U.S. Ser. No. 11/451,691, for all purposes, especially for all teachings regarding the formation of nucleic acid nanoball-loaded solid supports, these documents are incorporated herein by reference in their entirety.

In some embodiments, a DNB-loaded solid support is prepared using a patterned substrate with a two-dimensional array of spots. The spots are activated to capture and hold DNBs without leaving a DNB in the area between the spots. In general, the DNBs on the spots will repel other DNBs, resulting in only one DNB per spot. The share of DNB on solid support generally exceeds 90%, but may vary from 50% to 100%.

In other embodiments, the patterned surface is made using standard silicon processing techniques. This patterned array produces a higher density of DNBs than un-patterned arrays, resulting in per base readings with fewer pixels, faster reaction processes, and increased reagent use efficiency. In yet another embodiment, the patterned substrate is a 25 mm×75 mm (1"×3") standard microscope slide, each slide may accommodate about 1 billion independent spots capable of binding DNB. It should be understood that the present invention comprises higher density slides. In these embodiments, since the DNBs are set on the surface and then attached to the activated spots, the high-density DNB array is essentially "self-assembled" from the DNB in solution, thereby avoiding one of the most expensive aspects for preparation of traditional patterned oligo-arrays or DNA arrays.

In some embodiments, the surface of solid support may carry reactive functional groups that react with complementary functional groups on the polynucleotide molecule to form covalent bonds, for example, it may be performed by using the same technique used to attach cDNA to microarray; see, for example, Smirnov et al. (2004), Genes, Chromosomes & Cancer, 40: 72-77 and Beaucage (2001), Current Medicinal Chemistry, 8: 1213_1244, both of which are incorporated herein by reference. The DNB can also be effectively attached to a hydrophobic surface, such as a clean glass surface with a low concentration of various reactive functional groups (e.g., —OH groups). The attachment via a covalent bond formed between a polynucleotide molecule and a reactive functional group on the surface is also referred to herein as "chemical attachment."

In other embodiments, the polynucleotide molecules can be adsorbed onto a surface. In this embodiment, the polynucleotide is immobilized on the surface through a non-specific interaction, or through a non-covalent interaction such as hydrogen bond, van der Waals force, and the like.

The attachment may also comprise washing steps of various stringent conditions to remove incompletely attached individual molecules or other reagents from the previous preparation steps, wherein the presence of these individual molecules or reagents is not desired or they bind non-specifically to the surface.

There are many types of supports that can be utilized to form a random array with DNB, for example, the solid supports as described above. In one aspect, the support is a rigid solid with a surface, preferably a substantially planar area, so that the single molecules to be interrogated are in the same plane. The latter characteristic allows efficient signal collection by, for example, detection optics. In another aspect, the support comprises beads, in which case the surface of the beads contains reactive functional groups or capture probes that can be used to immobilize a polynucleotide molecule.

In yet another aspect, the solid support of the present invention is non-porous, especially when the single-molecule random array is analyzed by a hybridization reaction and requires a small volume. Suitable solid support materials include materials such as glass, polyacrylamide-coated glass, ceramics, silica, silicon, quartz, various plastics, and the like. The area of the planar area can be in the range of 0.5 to 4 cm$^2$. In one aspect, the solid support is glass or quartz, such as a microscope slide with a uniform silanized surface. This can be achieved using conventional test protocols, such as immersing in a solution of 3-glycidyl ether oxypropyltrimethoxysilane, N,N-diisopropylethylamine and anhydrous xylene (8: 1: 24, v/v) at 80° C. after acid treatment, so as to form an epoxy silanized surface (e.g., Beattie et al. (1995), Molecular Biotechnology, 4: 213). For example, by providing a 3' or 5' tri(ethylene glycol)phosphoryl spacer arm to a capturing oligonucleotide before application to the surface (see, Beattie et al., idem), such surface can be easily treated so as to be attached by the capturing oligonucleotide end. Other embodiments for functionalizing and further preparing the surface for use in the present invention are described in, for example, US patent applications U.S. Ser. No. 60/992,485, U.S. 61/026,337, U.S. 61/035,914, U.S. 61/061,134, U.S. 61/116,193, U.S. 61/102,586, U.S. Ser. No. 12/265,593, U.S. Ser. No. 12/266,385, U.S. Ser. No. 11/938,096, U.S. Ser. No. 11/981,804, U.S. Ser. No. 11/981,797, U.S. Ser. No. 11/981,793, U.S. Ser. No. 11/981,767, U.S. Ser. No. 11/981,761, U.S. Ser. No. 11/981,730, U.S. Ser. No. 11/981,685, U.S. Ser. No. 11/981,661, U.S. Ser. No. 11/981,607, U.S. Ser. No. 11/981,605, U.S. Ser. No. 11/927,388, U.S. Ser. No. 11/927,356, U.S. Ser. No. 11/679,124, U.S. Ser. No. 11/541,225, U.S. Ser. No. 10/547,214, U.S. Ser. No. 11/451,692, and U.S. Ser. No. 11/451,691, for all purposes, especially for all teachings related to the preparation of solid supports to form nucleic acid arrays and all teachings related to the formation of nucleic acid arrays, especially DNB arrays, these documents are incorporated herein by reference in their entirety.

In embodiments of the present invention involving patterned substrates, such patterns can be produced on a variety of surfaces using photolithography, electron beam lithography, nanoimprint lithography, and nanoprinting; see, for example, U.S. Pat. No. 5,143,854 to Pirrung et al., U.S. Pat. No. 5,774,305 to Fodor et al., Guo, (2004) Journal of Physics D: Applied Physics, 37: R123-141, which are incorporated herein by reference.

In one aspect, the surface of the patterned substrate is manufactured by photolithography. A commercially available optical planar quartz substrate is spin-coated with a 100 to 500 nm thick photoresist layer. The photoresist layer is then sintered onto the quartz substrate. By using a stepper, a reticle image with a region pattern to be activated is projected onto the surface of the photoresist layer. After exposure, the photoresist layer is developed to remove areas of the projection pattern that are exposed to the UV source. This is achieved by plasma etching, a dry development technique that produces very fine details. The substrate is then baked to strengthen the remaining photoresist layer. After baking, the quartz wafer can be functionalized. The wafer is then subjected to vapor deposition of 3-aminopropyldimethylethoxysilane. By varying the monomer concentration and the exposure time of the substrate, the density of the amino-functional monomer can be strictly controlled. Only the areas of quartz that have been exposed to the plasma etch process can react with and capture the monomer. The substrate is then baked again to sinter a single layer of the amino-functional monomer onto the exposed quartz. After baking, the remaining photoresist can be removed with acetone. Because of the different adhesion chemistry of the photoresist and the silane, the aminosilane-functionalized areas on the substrate remains intact during the acetone cleaning process. These areas can be further functionalized by reaction with P-phenylene-diisothiocyanate dissolved in a solution of pyridine and N,N-dimethylformamide. The substrate can then react with an amine-modified oligonucleotide. Alternatively, the oligonucleotide can be prepared using a 5'-carboxyl-modifier-C10 linker (Glen Research). This technology allows the oligonucleotide to be attached directly to the amine-modified support, thereby avoiding additional functionalization steps.

In another aspect, the surface of the patterned substrate is made by nano-imprint lithography (NIL). To prepare a DNA array, a quartz substrate is spin-coated with a photoresist layer, commonly referred to as a transfer layer. A second type of photoresist is then applied on the transfer layer, often called as an imprint layer. A main imprinting tool is then used to leave an indentation on the imprint layer. The total thickness of the imprint layer is then reduced by plasma etching until the lower areas of the imprint layer touch the transfer layer. Because the transfer layer is more difficult to remove than the imprint layer, it is substantially unaffected. The imprint layer and the transfer layer are then hardened by heating. The substrate is then placed in a plasma etcher until the lower areas of the imprint layer touch the quartz. The substrate is then derivatized by vapor deposition as described above.

In another aspect, the surface of the patterned substrate is made by nanoprinting. This process uses light, imprint or electron beam marking to produce a master mold, which is a negative image of the feature pattern required on the print head. The print head is usually made of a soft and flexible polymer such as polydimethylsiloxane (PDMS). This material or material layer with different properties is spin-coated onto a quartz substrate. Then, under a controlled temperature and pressure condition, the feature pattern is embossed to the surface layer of the photoresist material with the mold. The print head is then subjected to a plasma-based etching process in order to improve the aspect ratio of the print head and eliminate deformation of the print head due to the relaxation of the embossed material over time. The random array substrate is made using nanoprinting by leaving amine-modified oligonucleotide patterns on a homogeneously derivatized surface. These oligonucleotides will serve as capture probes for RCR products. One possible advantage of nanoprinting is the ability to print interlaced patterns of different capture probes onto a random array support. This can be achieved by successive printing with multiple print heads, wherein each print head carries a different pattern, and all patterns fit together to form the final support pattern with the structure. This type of method allows a localization coding of DNA elements in a random array. For example, a control concatemer containing a specific sequence can be bound to a random array at regular intervals.

In yet another aspect, a sub-micron-sized high-density array of spots for capturing oligonucleotides is prepared using a print head or imprint-master, wherein the print head or imprint master is composed of one or more beams of approximately 10,000 to 100 million optical fibers containing a core and a covering material. The fiber is drawn and fusion-spliced to produce a unique material that contains mandrels of approximately 50-1000 nm, separated by a coating material of a similar size or 2-5 times larger. A nanoprinting head containing a very large number of nanoscale posts is obtained by differential etching (dissolution) of the coating material. This print head can be used to place oligonucleotides or other biological (proteins, oligopeptides, DNA, aptamers) or chemical compounds, such as silanes with various reactive groups. In one embodiment, glass fiber tools are used as a patterned support to store oligonucleotides or other biological or chemical compounds. In this case, only the small posts produced by etching can come into contact with the material to be stored. A flat-cut fused fiber bundle can be used to guide light through the mandrels, so that light-induced chemical processes are only allowed to occur on the surface of the mandrel head, and no etching is required. In both cases, the same support can then be used as a light guide/collection device for imaging fluorescent labels used for labeling oligonucleotides or other reactants. This device provides a large field of view with a large numerical aperture (possibly >1). Imprints or printing tools that implement the storage of active materials or oligonucleotides can be used to print 2 to 100 different oligonucleotides in an interlaced pattern. This process requires precise positioning of the print head at approximately 50-500 nm. This type of oligonucleotide array can be used to attach 2 to 100 different DNA populations, such as different source DNAs. They can also be used to read sub-light-resolution spots in parallel by using DNA-specific anchors or tags. Information can be obtained through DNA-specific tags (for example, 16 specific anchors for 16 types of DNA), and 2 bases can be read through a combination of 5 to 6 colors and using 16 connection loops or one connection loop and 16 decoding loops. This method of preparing an array is effective if only a limited amount of information is needed for per fragment (for example, a small number of cycles), so that each cycle can provide more information or each surface can do more cycles.

As described above, in one embodiment of the invention, the DNB may be disposed or "loaded" on a patterned surface to form a high-density DNB array.

According to one embodiment, the DNB formulation is loaded into a flow slide, as described in Drmanac et al., Science 327: 78-81, 2010. Briefly, a slide is loaded by pipetting DNB onto the slide. For example, 2 to 3 times more DNB than the binding sites can be pipetted onto the slide. The loaded slide is incubated at 23° C. for 2 hours, rinsed to neutralize pH and remove unbound DNB.

The DNB prepared according to the method described above brings advantages in identifying the sequence of a target nucleic acid, because the DNB usually contains an adaptor (meaning an oligonucleotide with a known sequence, and a detailed description of the DNB containing an adaptor can be found in, for example, international patent application WO2013066975), which provides a known sequence point that can be easily sequenced when combined with a method using a sequencing primer. In addition, the DNB avoids the costs and problems of relying on a single fluorophore detection used by a single molecular sequencing system, as multiple copies of the target sequence are present in a single DNB.

The method of using a DNB according to the present invention comprises sequencing a target nucleic acid and detecting a specific sequence in the target nucleic acid (e.g., detecting a specific target sequence (e.g., a specific gene) and/or identifying and/or detecting a SNP). The method described herein can also be used to detect nucleic acid rearrangement and copy number change. The method described herein can also be used to implement nucleic acid quantification, such as digitizing gene expression (i.e., analyzing the entire transcriptome-total mRNA present in a sample), and detection of the number of specific sequences or sequence groups in a sample. Although much of the discussion herein is directed to identifying a DNB sequence, it is understood that other non-concatermer nucleic acid constructs containing an adaptor can also be used in the embodiments described herein.

The solid support treated by the above method of the present invention can be used in various applications, for example, application for nucleic acid sequencing. Such solid support can also be used in association with a variety of biochemical assays, including, for example, nucleic acid hybridization, enzymatic reactions (e.g., using endonucleases (including restriction enzymes), exonucleases, kinases, phosphatases, ligases, etc.), nucleic acid synthesis, nucleic acid amplification (e.g., performed by polymerase chain reaction, rolling circle replication, whole genome amplification, multiple displacement amplification, etc.), and any other form of biochemical analysis known in the art in which a nucleic acid attached to a solid support is used.

In other embodiments, the present invention also provides a use of the partially double-stranded oligonucleotide or the group of partially double-stranded oligonucleotides as described herein for improving the stability of a nucleic acid (especially a nucleic acid nanoball) on a solid support. Preferably, the partially double-stranded oligonucleotide or the group of partially double-stranded oligonucleotides as described herein is hybridized to the nucleic acid on the solid support before or after the nucleic acid is loaded on the solid support, wherein the partially double-stranded oligonucleotide hybridize to the nucleic acid through the regions B and/or B'.

In other embodiments, the present invention also provides a use of poloxamer for improving the loading of a nucleic acid on a solid support, which comprises immobilizing the nucleic acid on the solid support in the presence of poloxamer and/or allowing the solid support to contact with a poloxamer-containing reagent after the nucleic acid is loaded on the solid support.

In other embodiments, the present invention also provides a solid support, on which a nucleic acid molecule is immobilized, and the nucleic acid molecule hybridizes to the partially double-stranded oligonucleotide or the group of partially double-stranded oligonucleotides as described herein, wherein the partially double-stranded oligonucleotide hybridizes to the nucleic acid molecule through the regions B and/or B'. In a preferred embodiment, the nucleic acid molecule is a nucleic acid nanoball, such as DNB.

The method for improving the loading and stability of a nucleic acid as described herein can have a variety of applications, including but not limited to, nucleic acid analysis, such as nucleic acid sequencing, nucleic acid hybridization tests, or enzyme-assisted nucleic acid tests. The method of the present invention can be used in association with a variety of biochemical analyses, including, for example, nucleic acid hybridization, enzymatic reactions (e.g., using endonucleases (including restriction enzymes), exonucleases, kinases, phosphatases, ligases, etc.), nucleic acid synthesis, nucleic acid amplification (e.g., performed by polymerase chain reaction, rolling circle replication, whole genome amplification, multiple displacement amplification, etc.), and any other form of biochemical analysis known in the art in which a nucleic acid attached to a solid support is used.

Therefore, in other embodiments, the present invention also provides a method for nucleic acid analysis, comprising: a) obtaining a solid support having a nucleic acid molecule immobilized thereon according to the method for improving the loading of a nucleic acid on a solid support described herein, and b) analyzing the nucleic acid molecule on the solid support. The nucleic acid analysis includes, but is not limited to, nucleic acid sequencing, nucleic acid hybridization tests, or enzyme-assisted nucleic acid tests. In a preferred embodiment, the nucleic acid molecule is a nucleic acid nanoball, such as DNB.

SPECIFIC MODELS FOR CARRYING OUT THE PRESENT INVENTION

The embodiments of the present invention will be described in detail below with reference to examples, but those skilled in the art will understand that the following examples are only used to illustrate the present invention, and should not be regarded as limiting the scope of the present invention. If the specific conditions are not indicated in the examples, the conventional conditions or the conditions recommended by the manufacturer are used. If the reagents or instruments used are not specified by the manufacturer, they are all conventional products that are commercially available.

Example 1

Conventional Loading of DNB

According to the manufacturer's instructions, a MGIeasy™ DNA library preparation kit (Shenzhen MGI Technology Co., Ltd.) was used to extract DNA from *E. coli* standard strains as raw materials to prepare a library for sequencing. Referring to the instructions of the BGISEQ-500 DNB Preparation Loading Kit (Shenzhen MGI Technology Co., Ltd., Art. No. 85-05531-00), the prepared DNB was loaded on the sequencing chip.

As described in Drmanacetal., Science 327: 78-81, 2010, the DNB was adsorbed onto a photo-etched surface-modified chip. Specifically, DNB was diluted to 5 ng/μl with DNB Load Buffer I, and then mixed with DNB Load Buffer II at a ratio of 3:1, added to a reagent tank containing the chip, incubated at room temperature for 60-90 min. The DLB I (DNB Load Buffer I) and DLB II (DNB Load Buffer II) were prepared with reference to the instructions of the BGISEQ-500 DNB preparation load kit (Shenzhen MGI Technology Co., Ltd., Art. No. 85-05531-00).

Figure 1:
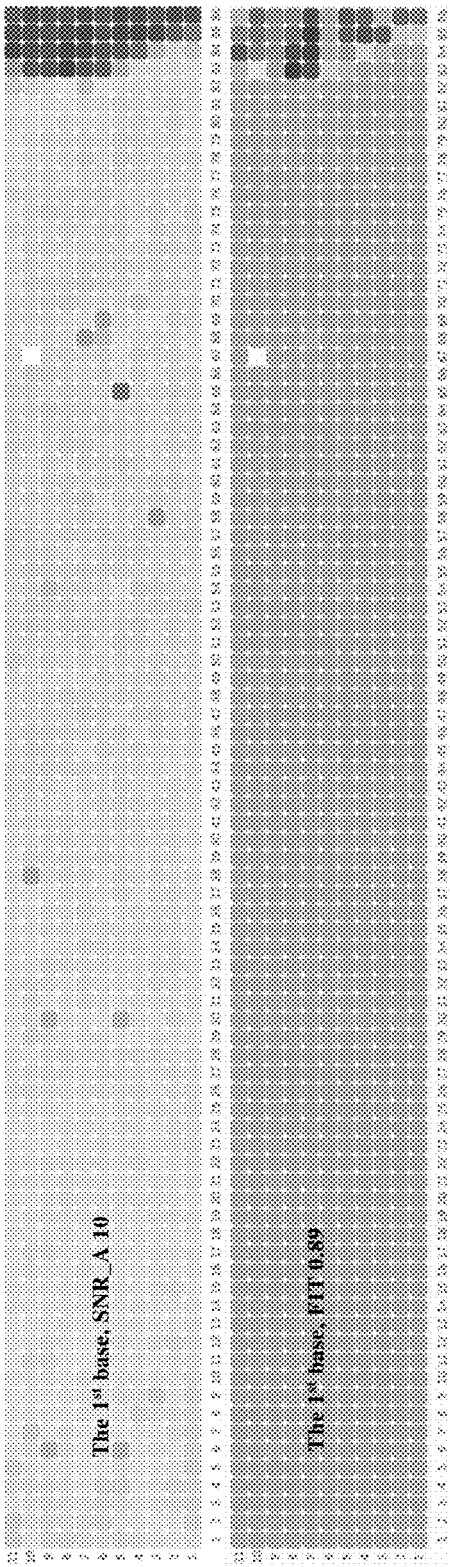
FIG. 1 shows a signal heat map for sequencing the first base using a conventional DNB-loaded chip.

After loading, the following steps were referred to carry out the post-loading processing of the chip. Specifically, the chip is not moved, the feeding and draining were performed simultaneously in the same reagent tank, the draining speed was as slow as possible, the rate was less than 62 μl/s, and the volume of the newly added reagent was 2-3 times the previous reagent volume. The operation was carried out by following the steps below. The used reagents referred to the Post Load Plate V3.0 in the BGISEQ-500 DNB Preparation Loading Kit (Shenzhen MGI Technology Co., Ltd., Cat. No. 85-05531-00).

a) DNB Rinse Buffer (DRB) was fed while DLB was drained, for about 2 min.

b) DNB Crash Buffer (DCB) was fed while DRB was drained, for about 5 min, c) Read Buffer (REB) was fed while DCB was drained, for about 2 min, d) Protein Wash Buffer (PWB) was fed while REB was drained, for about 8 min, e) DNB Crash Buffer (DCB) was fed while PWB was drained, for about 5 min, f) Read Buffer (REB) was fed while DCB was drained, for about 2 minutes, and this step was repeated once, g) The REB in the reagent tank was drained at the same speed, and the chip should still not move, h) Sequencing primer (SEQ ID NO: 1, 5'-CAA CTC CTT GGC TCA CAG AAC GAC ATG GCT ACG ATC CGA CTT-3') (aqueous solution, 2 ml) was slowly added, and incubated at room temperature for 20 min, 4) The processed chip was placed in Washing Reagent 2 for later use. The Washing Reagent 2 was derived from the BGISEQ-500 sequencing kit (SE50 V3.0, Shenzhen MGI Technology Co., Ltd., Art. No. PF-UM-PEV30), which was a washing reagent for washing the chip after the polymerization reaction, 5) One base was sequenced, the signal-to-noise ratio (SNR) and the base resolution (FIT) were analyzed by the program built-in the BGISEQ-500 sequencer (Shenzhen MGI Technology Co., Ltd.). As shown in FIG. 1, the first base (base A) as sequenced had an SNR value of 10 and a FIT value of 0.89, The specific sequencing steps were as follows: the chip was immersed in a polymerization reagent for about 1 minute, the chip was shifted out, then immersed in the Washing Reagent 2 for about 1 minute, the chip was shifted out, and then immersed in a protective reagent for about 1 minute, the chip was shifted out, and photographed for 20 to 30 minute to detect a fluorescent signal representing the identity information of base. The used reagents were from the BGISEQ-500 sequencing kit (SE50 V3.0, Shenzhen MGI Technology Co., Ltd., Art. No. PF-UM-PEV30), and the reaction conditions such as the temperature of each step and the photographing procedures were in accordance with the instructions of the kit as well as the standard procedures of the BGISEQ-500 sequencing platform.

Example 2

Improvement of DNB Loading by Poloxamer PF68

DNB was loaded using the same procedure as in Example 1, except that 0.2% of PF68 was added to the reagents (DRB, PWB, DCB, REB) for processing the chip after loading.

Specifically, the DNB was diluted to 5 ng/µl with DNB Load Buffer I, mixed with DNB Load Buffer II at a ratio of 3:1, added to a reagent tank containing a chip, and incubated at room temperature for 60-90 min.

Figure 2:
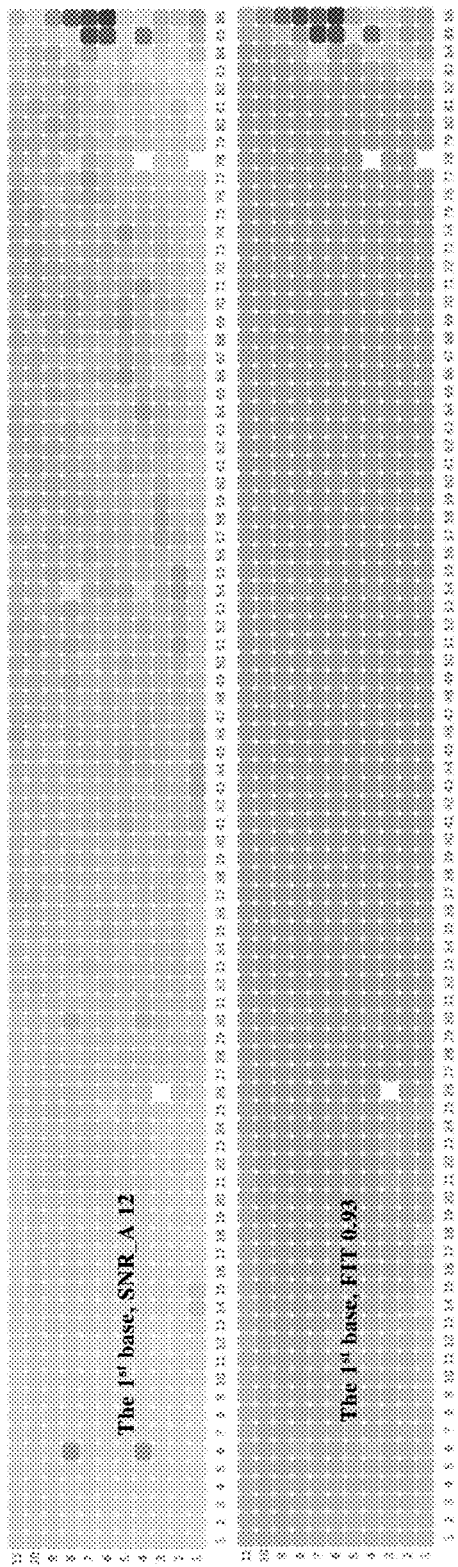
FIG. 2 shows a signal heat map for sequencing the first base using an improved DNB-loaded chip.

After loading, the chip is not moved, the feeding and draining were performed simultaneously in the same reagent tank, the draining speed was as slow as possible, the speed was less than 62 µl/s, and the volume of the newly added reagent was 2-3 times the previous reagent volume. The operation was carried out by following the steps below.

a) DRB was fed while DLB was drained, for about 2 min,
b) DCB was fed while DRB was drained, for about 5 min,
c) REB was fed while DCB was drained, for about 2 min,
d) PWB was fed while REB was drained, for about 8 min,
e) DCB was fed while PWB was drained, for about 5 min,
f) REB was fed while DCB was drained, for about 2 minutes, and this step was repeated once,
g) The REB in the reagent tank was drained at the same speed, and the chip should still not move,
h) Sequencing primer (SEQ ID NO: 1, 5'-CAA CTC CTT GGC TCA CAG AAC GAC ATG GCT ACG ATC CGA CTT-3') was slowly added, and incubated at room temperature for 20 min, 4) The processed chip was placed in Washing Reagent 2 for later use, 5) One base was sequenced as described in Example 1, the signal-to-noise ratio (SNR) and the base resolution (FIT) were analyzed by the program built-in the BGISEQ-500 sequencer (Shenzhen MGI Technology Co., Ltd.). As shown in FIG. 2, the first base (base A) as sequenced had a SNR value of 12 and a FIT value of 0.93. Such results showed that the addition of PF68 improved the loading of DNB.

In addition, the program built-in the sequencer was also used to analyze the change in signal intensity from the first base to the $15^{th}$ base. The specific steps for sequencing multiple bases were as follows: the chip was immersed in the polymerization reagent for about 1 minute, the chip was shifted out, then immersed in the Washing Reagent 2 for about 1 minute, the chip was shifted out, and then immersed in the protective reagent for about 1 minute, the chip was shifted out, photographed for 20-30 min to detect the fluorescence signal representing the identity information of base, then the chip was immersed in the regeneration reagent for about 1 min, the chip was shifted out, and then immersed in the Washing Reagent 1 for about 1 min, the chip was shifted out; then the previous steps were repeatedly applied to the chip to sequence the next base. The used reagents were from the BGISEQ-500 sequencing kit (SE50 V3.0, Shenzhen MGI Technology Co., Ltd., Art. No. PF-UM-PEV30), and the reaction conditions such as the temperature of each step and the photographing procedures were in accordance with the instructions of the kit and the standard procedures of the BGISEQ-500 sequencing platform. After a high-temperature reaction at 55° C., the DNB state became worse, and the signal was reduced by 60%, especially at the upper end of the chip.

Figure 3:
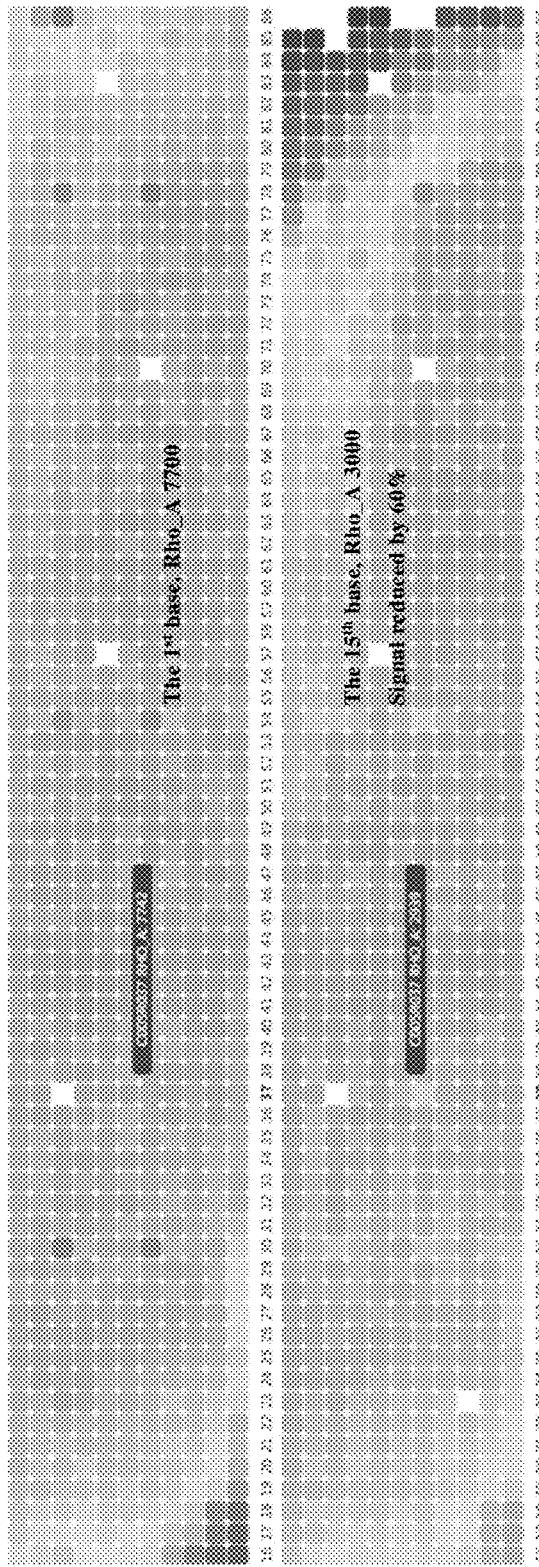
FIG. 3 shows a comparison of the decrease in signal value (Rho) after sequencing 15 bases using a DNB-loaded chip.

As shown in FIG. 3, the signal value (Rho) of the $15^{th}$ base in sequencing was reduced by about 60% in comparison with the signal value of the Pt base in sequencing. Especially at the top of the chip (right side of FIG. 3), the signal value was significantly affected.

In addition, the BGISEQ-500 sequencing kit (SE50 V3.0, Shenzhen MGI Technology Co., Ltd., Art. No. PF-UM-PEV30) was also used to load the chip into the BGISEQ-500 sequencer (Shenzhen MGI Technology Co., Ltd.) to complete the sequencing of one base, similarly indicating that the addition of PF68 improved DNB loading (results not shown).

Example 3

Improvement of DNB Loading by Poloxamer PF127

DNB was loaded using the same procedure as in Example 1, except that 0.5% of PF127 was added to the reagents (DRB, PWB, DCB, REB) for processing the chip after loading.

Specifically, the DNB was diluted to 5 ng/µl with DNB Load Buffer I, mixed with DNB Load Buffer II at a ratio of 3:1, added to a reagent tank containing a chip, incubated at room temperature for 60-90 min.

Figure 4:
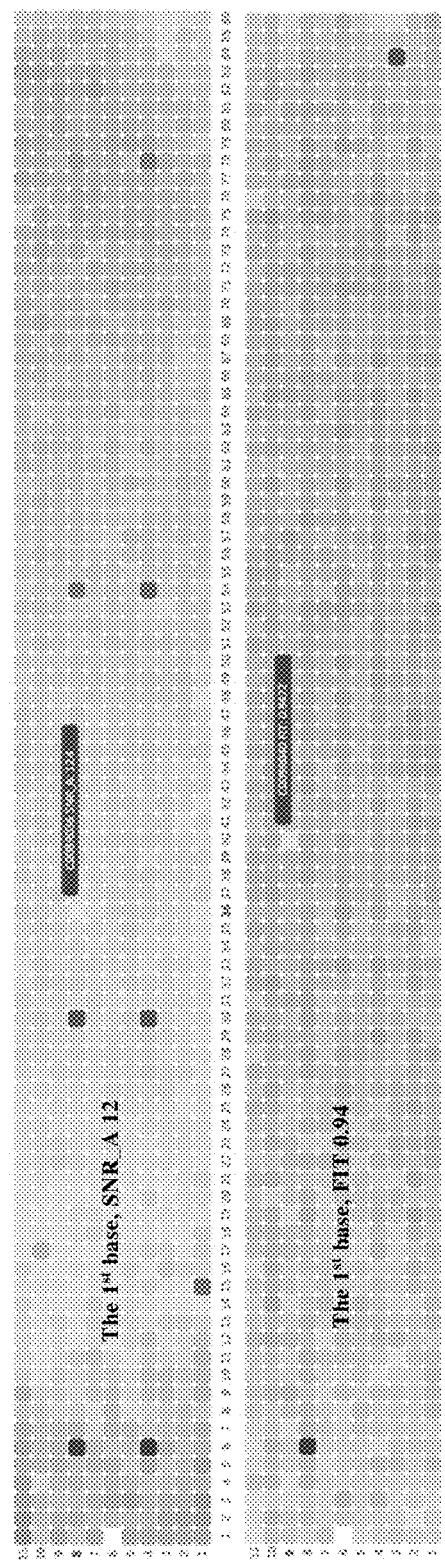
FIG. 4 shows a signal heat map for sequencing the first base using an improved DNB-loaded chip.

After loading, the chip is not moved, the feeding and draining were performed simultaneously in the same reagent tank, the draining speed was as slow as possible, the speed was less than 62 µl/s, and the volume of the newly added reagent was 2-3 times the previous reagent volume. The operation was carried out by following the steps below.

a) DRB was fed while DLB was drained, for about 2 min,
b) DCB was fed while DRB was drained, for about 5 min,
c) REB was fed while DCB was drained, for about 2 min,
d) PWB was fed while REB was drained, for about 8 min,
e) DCB was fed while PWB was drained, for about 5 min,
f) REB was fed while DCB was drained, for about 2 minutes, and this step was repeated once,
g) The REB in the reagent tank was drained at the same speed, and the chip should still not move,
h) Sequencing primer (SEQ ID NO: 1, 5'-CAA CTC CTT GGC TCA CAG AAC GAC ATG GCT ACG ATC CGA CTT-3') was slowly added, and incubated at room temperature for 20 min, 4) The processed chip was placed in Washing Reagent 2 for later use, 5) One base was sequenced as described in Example 1, the signal-to-noise ratio (SNR) and the base resolution (FIT) for each base were analyzed by the program built-in the BGISEQ-500 sequencer (Shenzhen MGI Technology Co., Ltd.). As shown in FIG. 4, the first base (base A) as sequenced had a SNR value of 12 and a FIT value of 0.94. Such results showed that the addition of PF127 improved the loading of DNB, which is similar to the result of PF68.

In addition, the BGISEQ-500 sequencing kit (SE50 V3.0, Shenzhen MGI Technology Co., Ltd., Art. No. PF-UM-PEV30) was also used to load the chip into the BGISEQ-500 sequencer (Shenzhen MGI Technology Co., Ltd.) to complete the sequencing of one base, similarly indicating that the addition of PF127 improved DNB loading (results not shown).

Example 4

Effect of TritonX-100 on DNB Loading

DNB was loaded using the same procedure as in Example 1, except that 0.1% TritonX-100 was added to the reagents (DRB, DCB, PWB, REB) for processing the chip after loading.

Specifically, the DNB was diluted to 5 ng/μl with DNB Load Buffer I, mixed with DNB Load Buffer II at a ratio of 3:1, added to a reagent tank containing a chip, incubated at room temperature for 60-90 min.

Figure 5:
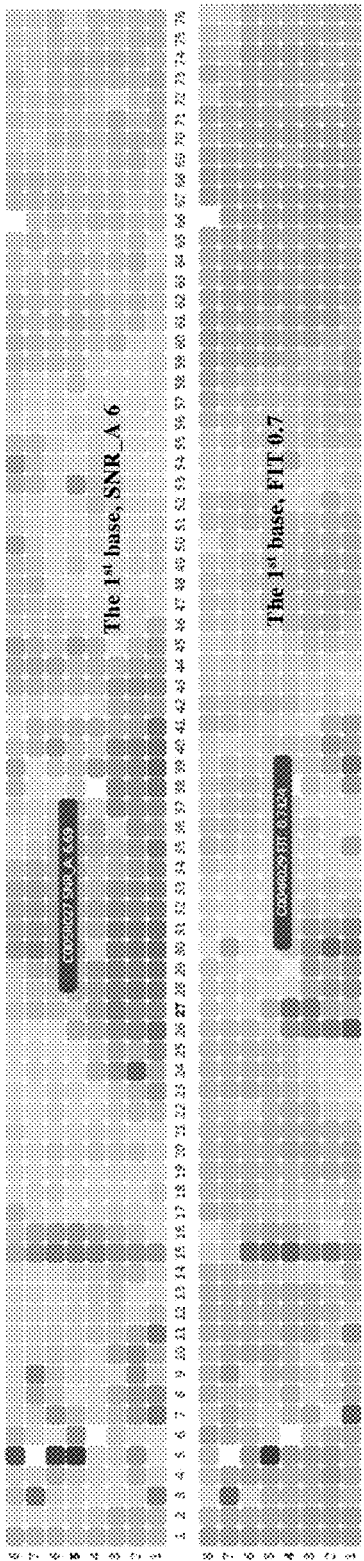
FIG. 5 shows the effect of TritonX-100 on DNB loading.

After loading, the chip is not moved, the feeding and draining were performed simultaneously in the same reagent tank, the draining speed was as slow as possible, the speed was less than 62 μl/s, and the volume of the newly added reagent was 2-3 times the previous reagent volume. The operation was carried out by following the steps below.

a) DRB was fed while DLB was drained, for about 2 min,
b) DCB was fed while DRB was drained, for about 5 min,
c) REB was fed while DCB was drained, for about 2 min,
d) PWB was fed while REB was drained, for about 8 min,
e) DCB was fed while PWB was drained, for about 5 min,
f) REB was fed while DCB was drained, for about 2 minutes, and this step was repeated once,
g) The REB in the reagent tank was drained at the same speed, and the chip should still not move.
h) Sequencing primer (SEQ ID NO: 1, 5'-CAA CTC CTT GGC TCA CAG AAC GAC ATG GCT ACG ATC CGA CTT-3') was slowly added, and incubated at room temperature for 20 min, 4) The processed chip was placed in Washing Reagent 2 for later use, 5) One base was sequenced as described in Example 1, the signal-to-noise ratio (SNR) and the base resolution (FIT) were analyzed by the program built-in the BGISEQ-500 sequencer (Shenzhen MGI Technology Co., Ltd.). As shown in FIG. 5, the first base (base A) as sequenced had a SNR value of 6 and a FIT value of 0.7. This showed that the addition of TritonX-100 not only did not improve the loading of DNB, but made the loading effect of DNB worse, and the phenomenon of uneven DNB on the chip was also obvious. Such results proved that the role of poloxamer in improving DNB loading was unique.

Example 5

Improvement of DNB Stability by the Partially Double-Stranded Oligonucleotides of the Invention DNB was loaded using the same procedure as in Example 1, except that two kinds of partially double-stranded oligonucleotides were used to replace the sequencing primer, that were, Oligonucleotide 1 and Oligonucleotide 2.

Oligonucleotide 1 and Oligonucleotide 2 were each formed by mixing and hybridizing two oligonucleotide strands having the same sequence under normal temperature conditions.

The sequence of the two oligonucleotide strands of Oligonucleotide 1 was:

(SEQ ID NO: 2)
5-GCCGTGCCACTGCGTGCGTCGACGGATGCGGCGGTCTCATGAGACCGC

CGCAACTCCTTGGCTCACAGAACGACATGGCTACGATCCGACTT-3.

The sequence of the two oligonucleotide strands of Oligonucleotide 2 was:

(SEQ ID NO: 3)
5-CATCCGTCGACGCACGCAGTGGCACGGCGGCACGTACTAGTACGTGCC

CAACTCCTTGGCTCACAGAACGACATGGCTACGATCCGACTT-3.

Figure 7:
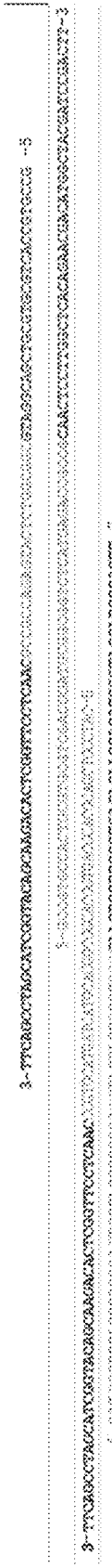
FIG. 7 shows the exemplary structure of the partially double-stranded oligonucleotides of the invention. From top to bottom: SEQ ID NO 2, SEQ ID NO: 2, SEQ ID NO: 3, SEQ ID NO: 3.

Oligonucleotide 1 and Oligonucleotide 2 could be mixed and hybridized at a concentration ratio of 1:1 under normal temperature conditions to form the structure shown in FIG. 7.

Specifically, the DNB was diluted to 5 ng/μl with DNB Load Buffer I, mixed with DNB Load Buffer II at a ratio of 3:1, added to a reagent tank containing a chip, and incubated at room temperature for 60-90 min.

Figure 6:
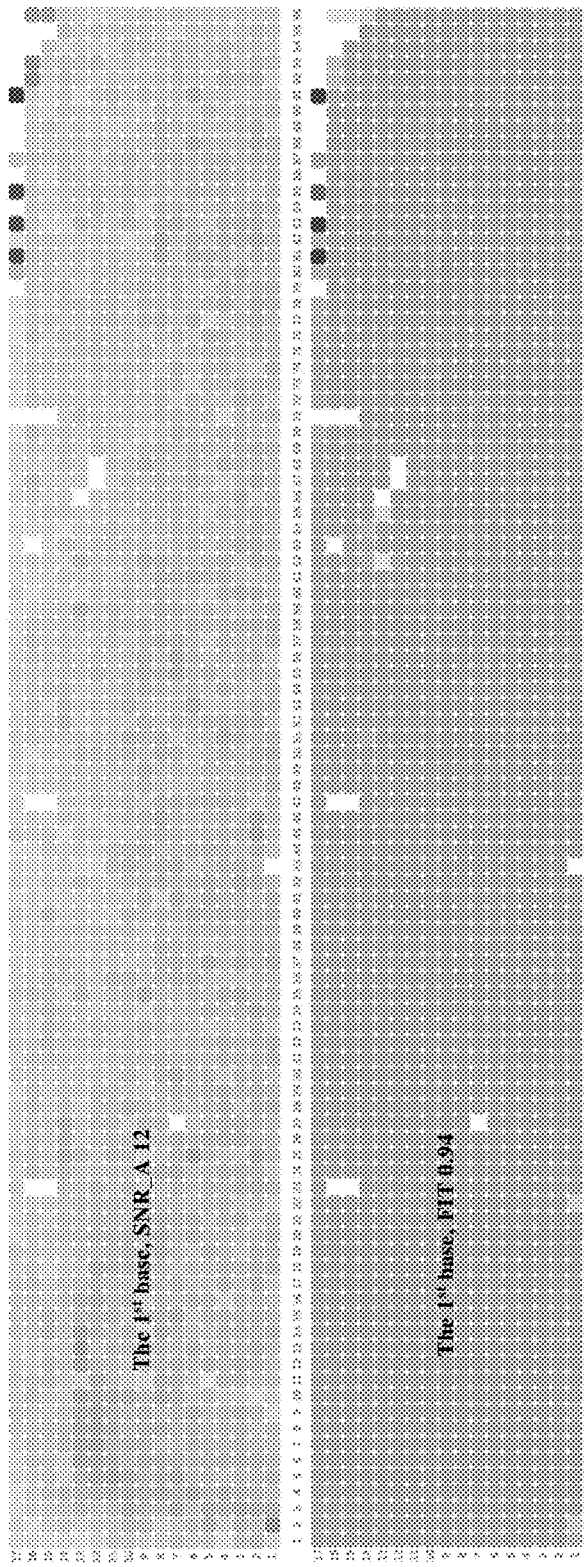
FIG. 6 shows the effect of the partially double-stranded oligonucleotides of the invention on DNB loading.
Figure 6:
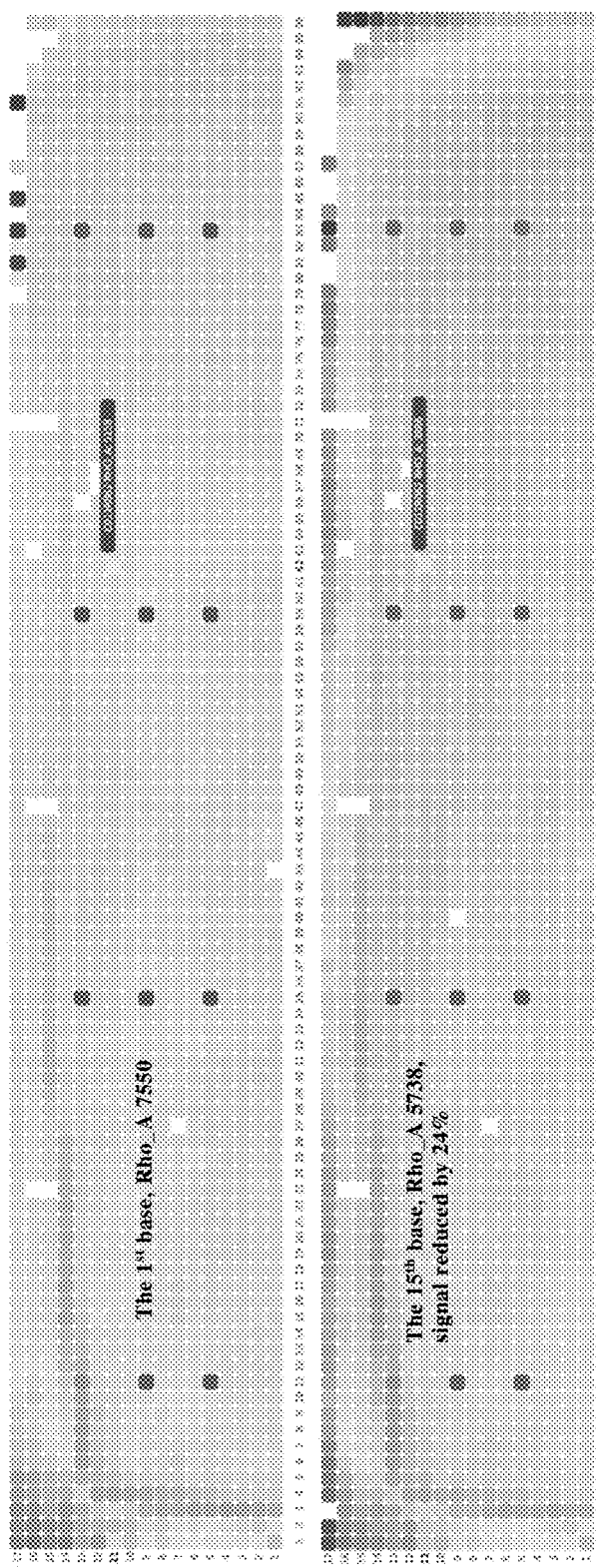

After loading, the chip is not moved, the feeding and draining were performed simultaneously in the same reagent tank, the draining speed was as slow as possible, the speed was less than 62 μl/s, and the volume of the newly added reagent was 2-3 times the previous reagent volume. The operation was carried out by following the steps below. DRB, PWB, DCB, and REB were all added with 0.2% PF68.

a) DRB was fed while DLB was drained, for about 2 min,
b) DCB was fed while DRB was drained, for about 5 min,
c) REB was fed while DCB was drained, for about 2 min,
d) PWB was fed while REB was drained, for about 8 min,
e) DCB was fed while PWB was drained, for about 5 min,
f) REB was fed while DCB was drained, for about 2 minutes, and this step was repeated once,
g) The REB in the reagent tank was drained at the same speed, and the chip should still not move,
h) Oligonucleotide 1 and Oligonucleotide 2 at a concentration ratio of 1:1 were slowly added, and incubated at room temperature for 20 min, 4) The processed chip was placed in Washing Reagent 2 for later use, 5) One base was sequenced as described in Example 1, the signal-to-noise ratio (SNR) and the base resolution (FIT) were analyzed by the program built-in the BGISEQ-500 sequencer (Shenzhen MGI Technology Co., Ltd.). As shown in FIG. 6, the first base (base A) as sequenced had a SNR value of 12 and a FIT value of 0.94. Furthermore, the program of the sequencer was used to analyze the change in signal intensity from the first base to the $15^{th}$ base. The results were shown in FIG. 6. The signal value (Rho) of the $15^{th}$ base in sequencing was reduced by about 24% compared to the signal value of the $1^{st}$ base in sequencing, and the signal value on the entire chip, especially on the upper end of the chip (FIG. 6, right) was not significantly affected. Such results showed that the use of the partially double-stranded oligonucleotides of the invention significantly improved the robustness of DNB loading, and that the stability of DNB during sequencing is significantly improved.

In addition, the BGISEQ-500 sequencing kit (SE50 V3.0, Shenzhen MGI Technology Co., Ltd., Art. No. PF-UM-PEV30) was also used to load the chip into the BGI-SEQ500 sequencer (Shenzhen MGI Technology Co., Ltd.) to complete the sequencing of 15 bases, similarly indicating that the use of the partially double-stranded oligonucleotides of the invention improved the stability of DNB (results not shown).

sequence, wherein the first oligonucleotide strand and the second oligonucleotide strand hybridize to each other through the regions A and A', thereby forming the partially double-stranded oligonucleotide;

wherein the region C of at least one partially double-stranded oligonucleotide is reversely complementary to the region C of at least one other partially double-stranded oligonucleotide such that at least two partially

What is claimed is:

1. A method for improving loading of a nucleic acid nanoball on a solid support, comprising a) providing a solid support having a nucleic acid immobilized thereon, and b) allowing the solid support to contact with a poloxamer-containing reagent.

2. A group of partially double-stranded oligonucleotides, comprising at least two partially double-stranded oligonucleotides,
wherein the partially double-stranded oligonucleotide comprising a first oligonucleotide strand and a second oligonucleotide strand, wherein the first oligonucleotide strand comprises a region C, a region A and a region B from 5' to 3', and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence, wherein the first oligonucleotide strand and the second oligonucleotide strand hybridize to each other through the regions A and A', thereby forming the partially double-stranded oligonucleotides can hybridize to each other through the respective region C; and
wherein the regions A and A' are 10-40 nucleotides in length; the regions B and B' are 10-70 nucleotides in length; and, the regions C and C' are 10-70 nucleotides in length.

3. The group of partially double-stranded oligonucleotides according to claim 2, wherein the first oligonucleotide strand comprises a region C, a region A and a region B from 5' to 3', and the second oligonucleotide strand comprises a region C', a region A' and a region B' from 5' to 3', wherein the regions A and A' are reversely complementary to each other, and the regions B and B' are not complementary to each other but each is complementary to a predetermined target sequence, wherein the first oligonucleotide strand and the second oligonucleotide strand hybridize to each other through the regions A and A', thereby forming the partially double-stranded oligonucleotide, wherein at least one of the regions C and C' of at least one partially double-stranded oligonucleotide is reversely complementary to at least one of the regions C and C' of at least one other partially double-stranded oligonucleotide such that at least two partially double-stranded oligonucleotides are capable of hybridizing to each other through the respective regions C and/or C'.

4. The group of partially double-stranded oligonucleotides according to claim 3, wherein the group of partially double-stranded oligonucleotides is characterized by one or more of the following:
(1) the regions C and C' have the same or different sequences,
(2) the regions B and B' are designed to be complementary to the same target sequence, or the regions B and B' are designed to be complementary to different target sequences,
(3) the regions A and A' are 15-30 nucleotides in length,
(4) the regions B and B' are 30-42 nucleotides in length, and
(5) the regions C and C' are 20-50 nucleotides in length.

5. A method for improving stability of a nucleic acid on a solid support, wherein,
the method comprises the steps of: a) providing a solid support having a nucleic acid molecule immobilized thereon; and b) allowing a partially double-stranded oligonucleotide or a group of partially double-stranded oligonucleotides to hybridize to the nucleic acid molecule on the solid support,
wherein, the partially double-stranded oligonucleotide comprises a first oligonucleotide strand and a second oligonucleotide strand, wherein the first oligonucleotide strand comprises a region C, a region A and a region B from 5' to 3'; and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence; wherein the first oligonucleotide strand and the second oligonucleotide strand hybridize to each other through the regions A and A', thereby forming the partially double-stranded oligonucleotide;
wherein the group of partially double-stranded oligonucleotides comprise at least two partially double-stranded oligonucleotides;
wherein the partially double-stranded oligonucleotide hybridizes to the nucleic acid molecule through the regions B and/or B',
or
the method comprises the steps of: a) providing a nucleic acid molecule; b) allowing a partially double-stranded oligonucleotide or the group of partially double-stranded oligonucleotides to hybridize to the nucleic acid molecule,
wherein, the partially double-stranded oligonucleotide comprises a first oligonucleotide strand and a second oligonucleotide strand, wherein the first oligonucleotide strand comprises a region C, a region A and a region B from 5' to 3'; and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence; wherein the first oligonucleotide strand and the second oligonucleotide strand hybridize to each other through the regions A and A', thereby forming the partially double-stranded oligonucleotide;
wherein the group of partially double-stranded oligonucleotides comprise at least two partially double-stranded oligonucleotides;
wherein the partially double-stranded oligonucleotide hybridizes to the nucleic acid molecule through the regions B and/or B'; and c) immobilizing the nucleic acid molecule on a solid support.

6. A method for improving loading and stability of a nucleic acid on a solid support, wherein,
the method comprises the steps of: a) providing a solid support having a nucleic acid molecule immobilized thereon; and b) allowing the solid support to contact with a poloxamer-containing reagent; and c) allowing a partially double-stranded oligonucleotide or a group of partially double-stranded oligonucleotides to hybridize to the nucleic acid molecule on the solid support,
wherein, the partially double-stranded oligonucleotide comprises a first oligonucleotide strand and a second oligonucleotide strand, wherein the first oligonucleotide strand comprises a region C, a region A and a region B from 5' to 3'; and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence; wherein the first oligonucleotide strand and the second oligonucleotide strand hybridize to each other through the regions A and A', thereby forming the partially double-stranded oligonucleotide;
wherein the group of partially double-stranded oligonucleotides comprise at least two partially double-stranded oligonucleotides;
wherein the partially double-stranded oligonucleotide hybridizes to the nucleic acid molecule through the regions B and/or B'; wherein step c) is performed before or after step b);
or,
the method comprises the steps of: a) providing a nucleic acid molecule; b) allowing a partially double-stranded oligonucleotide or a group of partially double-stranded oligonucleotides to-hybridize to the nucleic acid molecule,
wherein, the partially double-stranded oligonucleotide comprises a first oligonucleotide strand and a second oligonucleotide strand, wherein the first oligonucleotide strand comprises a region C, a region A and a region B from 5' to 3'; and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence; wherein the first oligonucleotide strand and the second oligonucleotide strand hybridize to each other through the regions A and A', thereby forming the partially double-stranded oligonucleotide;
wherein the group of partially double-stranded oligonucleotides comprise at least two partially double-stranded oligonucleotides;
wherein the partially double-stranded oligonucleotide hybridizes to the nucleic acid molecule through the regions B and/or B'; c) immobilizing the nucleic acid molecule on a solid support; and d) allowing the solid support to contact with a poloxamer-containing reagent.

7. The method according to claim 1, wherein the method is characterized by one or more of the following:
   (1) the poloxamer is a hydrophilic poloxamer,
   (2) the poloxamer is a hydrophilic poloxamer having a HLB of 20-29 or a mixture thereof,
   (3) the poloxamer is selected from PF68, PF108, PF127, equivalents thereof, and mixtures thereof,
   (4) the poloxamer-containing reagent contains 0.01% to 2% (w/v) poloxamer,
   (5) the poloxamer-containing reagent contains 0.2% to 0.5% (w/v) poloxamer, and
   (6) the nucleic acid nanoball is a DNA nanoball.

8. The method according to claim 6, wherein the method is characterized by one or more of the following:
   (1) the poloxamer is a hydrophilic poloxamer,
   (2) the poloxamer is a hydrophilic poloxamer having a HLB of 20-29 or a mixture thereof,
   (3) the poloxamer is selected from PF68, PF108, PF127, equivalents thereof, and mixtures thereof,
   (4) the poloxamer-containing reagent contains 0.01% to 2% (w/v) poloxamer,
   (5) the poloxamer-containing reagent contains 0.2% to 0.5% (w/v) poloxamer,
   (6) the nucleic acid is a nucleic acid nanoball, and
   (7) the nucleic acid nanoball is a DNA nanoball.

9. A solid support, wherein a nucleic acid molecule is immobilized on the solid support, and the nucleic acid molecule hybridizes to a partially double-stranded oligonucleotide or a group of partially double-stranded oligonucleotides,
   wherein, the partially double-stranded oligonucleotide comprises a first oligonucleotide strand and a second oligonucleotide strand, wherein the first oligonucleotide strand comprises a region C, a region A and a region B from 5' to 3'; and the second oligonucleotide strand comprises a region A' and a region B' from 5' to 3', and optionally, further comprises a region C' at upstream of the region A'; wherein the regions A and A' are reversely complementary to each other, and the regions B and B' are not complementary to each other but each is complementary to a predetermined target sequence; wherein the first oligonucleotide strand and the second oligonucleotide strand hybridize to each other through the regions A and A', thereby forming the partially double-stranded oligonucleotide;
   wherein the group of partially double-stranded oligonucleotides comprise at least two partially double-stranded oligonucleotides;
   wherein the partially double-stranded oligonucleotide hybridizes to the nucleic acid molecule through the regions B and/or B'.

10. The solid support according to claim 9, wherein the nucleic acid is a nucleic acid nanoball or a DNA nanoball.

11. A method for nucleic acid analysis, comprising:
    a) obtaining a solid support having a nucleic acid nanoball immobilized thereon according to the method according to claim 1, and
    b) analyzing the nucleic acid nanoball on the solid support.

12. The method according to claim 11, wherein the method is characterized by one or more of the following:
    (1) the nucleic acid analysis is selected from nucleic acid sequencing, nucleic acid hybridization tests, or enzyme-assisted nucleic acid tests, and
    (2) the nucleic acid nanoball is a DNA nanoball.

13. A method for nucleic acid analysis, comprising:
    a) obtaining a solid support having a nucleic acid molecule immobilized thereon according to the method according to claim 5, and
    b) analyzing the nucleic acid molecules on the solid support.

14. The method according to claim 13, wherein the method is characterized by one or more of the following:
    (1) the nucleic acid analysis is selected from nucleic acid sequencing, nucleic acid hybridization tests, or enzyme-assisted nucleic acid tests,
    (2) the nucleic acid is a nucleic acid nanoball, and
    (3) the nucleic acid nanoball is a DNA nanoball.

15. A method for nucleic acid analysis, comprising:
    a) obtaining a solid support having a nucleic acid molecule immobilized thereon according to the method according to claim 6, and
    b) analyzing the nucleic acid molecules on the solid support.

16. The method according to claim 15, wherein the method is characterized by one or more of the following:
    (1) the nucleic acid analysis is selected from nucleic acid sequencing, nucleic acid hybridization tests, or enzyme-assisted nucleic acid tests,
    (2) the nucleic acid is a nucleic acid nanoball, and
    (3) the nucleic acid nanoball is a DNA nanoball.

17. The method according to claim 5, wherein the nucleic acid is a nucleic acid nanoball or a DNA nanoball.

18. The group of partially double-stranded oligonucleotides according to claim 2, wherein
    the region C or C' is designed such that when a first and a second partially double-stranded oligonucleotides are present, the region C or C' of the first partially double-stranded oligonucleotide is reversely complementary to the region C or C' of the second partially double-stranded oligonucleotide respectively, so that the first partially double-stranded oligonucleotide and the second partially double-stranded oligonucleotide can hybridize to each other through the respective region C or C', or
    the regions C and C' is designed such that when a first and a second partially double-stranded oligonucleotides are present, at least one of the regions C and C' of the first partially double-stranded oligonucleotide is reversely complementary to at least one of the regions C and C' of the second partially double-stranded oligonucleotide, so that the first partially double-stranded oligonucleotide and the second partially double-stranded oligonucleotide can hybridize to each other through the respective region C and/or C'.

19. The method of claim 5, wherein the group of the partially double-stranded oligonucleotides are subjected to hybridize to the nucleic acid molecule, wherein
    the region C or C' is designed such that when a first and a second partially double-stranded oligonucleotides are present, the region C or C' of the first partially double-stranded oligonucleotide is reversely complementary to the region C or C' of the second partially double-stranded oligonucleotide respectively, so that the first partially double-stranded oligonucleotide and the second partially double-stranded oligonucleotide can hybridize to each other through the respective region C or C', or
    the regions C and C' is designed such that when a first and a second partially double-stranded oligonucleotides are present, at least one of the regions C and C' of the first partially double-stranded oligonucleotide is reversely complementary to at least one of the regions C and C' of the second partially double-stranded oligonucleotide, so that the first partially double-stranded oligonucleotide and the second partially double-stranded oligonucleotide can hybridize to each other through the respective region C and/or C'.

20. The method of claim 6, wherein the group of the partially double-stranded oligonucleotides are subjected to hybridize to the nucleic acid molecule, wherein
 the region C or C' is designed such that when a first and a second partially double-stranded oligonucleotides are present, the region C or C' of the first partially double-stranded oligonucleotide is reversely complementary to the region C or C' of the second partially double-stranded oligonucleotide respectively, so that the first partially double-stranded oligonucleotide and the second partially double-stranded oligonucleotide can hybridize to each other through the respective region C or C', or
 the regions C and C' is designed such that when a first and a second partially double-stranded oligonucleotides are present, at least one of the regions C and C' of the first partially double-stranded oligonucleotide is reversely complementary to at least one of the regions C and C' of the second partially double-stranded oligonucleotide, so that the first partially double-stranded oligonucleotide and the second partially double-stranded oligonucleotide can hybridize to each other through the respective region C and/or C'.

* * * * *

SEQUENCE LISTING

```
<160> NUMBER OF SEQ ID NOS: 3

<210> SEQ ID NO 1
<211> LENGTH: 42
<212> TYPE: DNA
<213> ORGANISM: artificial
<220> FEATURE:
<223> OTHER INFORMATION: Primer

<400> SEQUENCE: 1
caactccttg gctcacagaa cgacatggct acgatccgac tt                              42

<210> SEQ ID NO 2
<211> LENGTH: 92
<212> TYPE: DNA
<213> ORGANISM: artificial
<220> FEATURE:
<223> OTHER INFORMATION: Oligonucleotide 1

<400> SEQUENCE: 2
gccgtgccac tgcgtgcgtc gacggatgcg gcggtctcat gagaccgccg caactccttg          60
gctcacagaa cgacatggct acgatccgac tt                                        92

<210> SEQ ID NO 3
<211> LENGTH: 90
<212> TYPE: DNA
<213> ORGANISM: artificial
<220> FEATURE:
<223> OTHER INFORMATION: Oligonucleotide 2

<400> SEQUENCE: 3
catccgtcga cgcacgcagt ggcacggcgg cacgtactag tacgtgccca actccttggc          60
tcacagaacg acatggctac gatccgactt                                           90
```